(12) United States Patent
Bayer et al.

(10) Patent No.: US 11,592,657 B2
(45) Date of Patent: Feb. 28, 2023

(54) METHOD AND SYSTEM FOR IDENTIFYING OBJECTS IN A BLOOD SAMPLE

(71) Applicant: Hemotech Cognition, LLC, Austin, TX (US)

(72) Inventors: Theodore F. Bayer, Austin, TX (US); Randall E. Wilcox, Orlando, FL (US); Patrick Walsh, Cary, NC (US)

(73) Assignee: Hemotech Cognition, LLC, Austin, TX (US)

( * ) Notice: Subject to any disclaimer, the term of this patent is extended or adjusted under 35 U.S.C. 154(b) by 70 days.

(21) Appl. No.: 17/351,346

(22) Filed: Jun. 18, 2021

(65) Prior Publication Data

US 2021/0333537 A1 Oct. 28, 2021

Related U.S. Application Data

(63) Continuation-in-part of application No. 16/719,360, filed on Dec. 18, 2019, now abandoned.

(60) Provisional application No. 62/781,168, filed on Dec. 18, 2018.

(51) Int. Cl.
| | | |
|---|---|---|
| *G01N 33/49* | (2006.01) | |
| *G02B 21/36* | (2006.01) | |
| *G06N 20/00* | (2019.01) | |
| *G06V 20/69* | (2022.01) | |

(52) U.S. Cl.
CPC ......... *G02B 21/367* (2013.01); *G01N 33/49* (2013.01); *G06N 20/00* (2019.01); *G06V 20/693* (2022.01)

(58) Field of Classification Search
CPC ...... G02B 21/367; G01N 33/49; G06N 20/00; G06N 3/08; G06V 20/693; G06V 2201/03; G06V 10/141; G06V 10/143; G06V 20/69; G06V 20/698; G06T 2207/10024; G06T 7/62; G06T 2207/10056; G06T 2207/20081; G06T 2207/30024; G06T 7/0012; C12Q 1/02

See application file for complete search history.

(56) References Cited

U.S. PATENT DOCUMENTS

| | | | |
|---|---|---|---|
| 2015/0118706 A1* | 4/2015 | Tateyama | C12Q 1/04 435/288.7 |
| 2015/0213599 A1 | 7/2015 | Buzaglo et al. | |
| 2018/0246313 A1 | 8/2018 | Eshel et al. | |
| 2020/0049599 A1 | 2/2020 | Alexander et al. | |
| 2020/0193596 A1 | 6/2020 | Bayer | |

* cited by examiner

*Primary Examiner* — Siamak Harandi
(74) *Attorney, Agent, or Firm* — Harness, Dickey & Pierce, P.L.C.

(57) ABSTRACT

A system and method for analyzing bodily fluid include a sample holder holding a bodily fluid sample, an image capture device generating an image of the bodily fluid sample comprising a plurality of fields of view. An image processor is programmed to determine a biofilm in the bodily fluid sample from the image, determine a biofilm area or volume within each of the plurality of fields of view to form a plurality of biofilm areas, determine a total biofilm area or total biofilm volume by adding the plurality of biofilm areas, determine a first value corresponding to a comparison of the total biofilm area or the total biofilm volume and a total volume of the bodily fluid sample, and classify the first value into a classification. An analyzer, using the classification, displays an indicator on a display for indicating the classification of the biofilm within the bodily fluid sample.

28 Claims, 20 Drawing Sheets

| INDICATOR | AMOUNT | VARIANCE |
|---|---|---|
| Sample Identifier | 12345 | X |
| Field Of View Analyzed | XX | X |
| Biofilm Occurrence Density Ratio | XX | X |
| Biofilm Density Ratio | XX | X |
| Average Confidence Score | XX | X |
| Biofilm Volume Weighted Confidence Score | XX | X |
| FOV Volume Weighted Confidence Score | XX | X |

METHOD AND SYSTEM FOR IDENTIFYING OBJECTS IN A BLOOD SAMPLE

CROSS-REFERENCE TO RELATED APPLICATIONS

This application is a continuation-in part of U.S. application Ser. No. 16/719,360 filed on Dec. 18, 2019, which claims the benefit of U.S. Provisional Application No. 62/781,168, filed on Dec. 18, 2018. The entire disclosure of the above application is incorporated herein by reference.

TECHNICAL FIELD

The present disclosure relates generally to blood content screening systems and, more specifically, to a method and system providing identifying and characterizing biofilm structures in a blood sample.

BACKGROUND

The statements in this section merely provide background information related to the present disclosure and may not constitute prior art.

Biofilms are found, for example, on the surface of stones in rivers and ponds, in water pipelines, as dental plaque on teeth and on surgical implants. Microorganisms within biofilms appear to be less susceptible to biocides than their planktonic counterparts. The extracellular polymer and/or nutrient limitation associated with the position of organisms in the biofilm may alter sensitivity. Biofilms allow for the rapid spread of genetic material between the component microorganisms. Biofilm formation can have serious implications in industrial, environmental, medical and public health situations It is important for doctors to be able to determine presence of biofilm a person may have. In addition, knowing the severity of the biofilm is also desirable. The use of cultures, antibodies, antigens or genetic material are often used in various tests.

Different types of bodily fluids may be examined such as blood, sputum, urine, stool, tissue, cerebral spinal fluid and mucus from the nose, throat or genital area.

Conventional analysis of bodily fluids may not be adequate for screening biofilms present in Lyme disease and other treatment resistant infections. Lyme disease is a blood borne disease with spirochete or biofilm present in Lyme disease samples. The identification of Lyme disease is often difficult.

SUMMARY

The present disclosure provides a way to analyze blood or other bodily fluids in an optical manner using a machine-learning model to detect biofilm objects or structures. Optical recognition in a bodily fluid such as blood is performed by a trained machine-learning model that recognizes the shapes, object or structures of biofilms. Biofilm is a non-moving object in bodily fluid. Discerning movement can be an important feature for the manual identification of some objects in blood or other bodily fluids. However, computer vision technology considers images independently, and is not aware of time nor motion. Therefore, in addition to recognizing static biofilm, a technique allow augmentation of images submitted by imparting a coloration feature to objects under motion. Colorization is done by combining three consecutively captured monochrome images into one color image by mapping each monochrome image into one of the three sets of primary color pixel/receptors. When the three monochrome images are of the same field of view, but taken at different times, our resultant color image will look the same as the monochrome except with coloration where there has been motion while taking the monochrome images.

In one aspect of the disclosure, a system includes a sample holder holding a bodily fluid sample, an image capture device generating an image of the bodily fluid sample comprising a plurality of fields of view. An image processor is programmed to determine a biofilm in the bodily fluid sample from the image, determine a biofilm area or volume within each of the plurality of fields of view to form a plurality of biofilm areas, determine a total biofilm area or total biofilm volume by adding the plurality of biofilm areas, determine a first value corresponding to a comparison of the total biofilm area or the total biofilm volume and a total volume of the bodily fluid sample, and classify the first value into a classification. An analyzer, in response to the classification, displays an indicator on a display for indicating the classification of the biofilm within the bodily fluid sample.

Aspects of the system include but are not limited by the indicator indicating the presence or non-presence of biofilm, a density of the biofilm within the bodily fluid sample, a severity based on the density of the biofilm, a volume of biofilm within the bodily fluid sample, and a volume weighted confidence score of the biofilm within the bodily fluid sample. The system may also include the image processor determining an average confidence level and the indicator comprises the average confidence level. The sample holder holds the sample in a well with cover and the well and cover comprises a predetermined sample volume. A position actuator positions the sample holder into the plurality of fields of view.

In another aspect, a method comprises generating an image of a bodily fluid sample comprising a plurality of fields of view, determining a biofilm in the bodily fluid sample from the image, determining a biofilm area or volume within each of the plurality of fields of view to form a plurality of biofilm areas, determining a total biofilm area or volume by adding the plurality of biofilm areas, determining a first value corresponding to a comparison of the total biofilm area or volume and a total volume of the bodily fluid sample, classifying the first value into a classification and, in response to the classification, displaying an indicator on a display for indicating the classification of the biofilm within the bodily fluid sample.

In yet another aspect of the disclosure, a system comprises a sample holder holding a bodily fluid sample comprising objects. An image capture device generating a first image of the objects and generating a second image of the objects after the first image and generating a third image of the objects after the second image. An image processor is programmed to color the objects in the first image with a first color to form a first colored image, color the objects in the second image with a second color to form a second colored image, color the objects in the third image with a third color to form a third colored image, add the first colored image, the second colored image and the third colored image to form a composite image of the object, determine movement of a first object based on the composite image, determining non-movement of a second object based on the composite image, classify the second object as a biofilm based on non-movement of the object to form a classification. An analyzer, displays an indicator on a display for indicating the classification of the biofilm within the bodily fluid sample.

In another aspect of the disclosure, a method comprises generating a first image of an object in bodily fluid, coloring the object in the first image with a first color to form a first colored image; generating a second image of the object later in time than the first image, coloring the object in the second image with a second color to form a second colored image, generating a third image of the object later in time than the second image, coloring the object in the third image with a third color to form a third colored image, adding the first colored image, the second colored image and the third colored image to form a composite image, determining movement of a first object based on the composite image, determining non-movement of a second object based on the composite image, classifying the second object as a biofilm based on non-movement of the object to form a classification and displaying an indicator on a display for indicating the classification of the biofilm within the bodily fluid sample.

Another aspect of the disclosure, a system for classifying a biofilm comprises a sample holder holding a bodily fluid sample. An image capture device generates a composite image of a plurality of images from a plurality of fields of view of the bodily fluid sample. The bodily fluid sample comprises a biofilm having a plurality of objects. An image processor programmed to determine a quantity of the fields of view, determine a biofilm occurrence density ratio, determine a biofilm density ratio, determine an average confidence score, determine a biofilm volume weighted confidence score and a field of view volume weighted confidence score. An analysis report generator generates a report comprising the biofilm occurrence density ratio, the biofilm density ratio, the average confidence score, the biofilm volume weighted confidence score and the field of view volume weighted confidence score.

In another aspect of the disclosure, a system comprises a sample holder holding a bodily fluid sample, and an image capture device generating a first image of an object, generating a second image of the object after the first image and generating a third image of the object after the second image. An image classifier is programmed to color the object in the first image with a first color to form a first colored image, color the object in the second image with a second color to form a second colored image, color the object in the third image with a third color to form a third colored image, add the first colored image, the second colored image and the third colored image to form a composite image, determine movement of the object based on the composite image; and classify the object based on movement of the object to form a classification. An analyzer, in response to the classification, displays an indicator on a display for indicating the classification within the bodily fluid sample.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
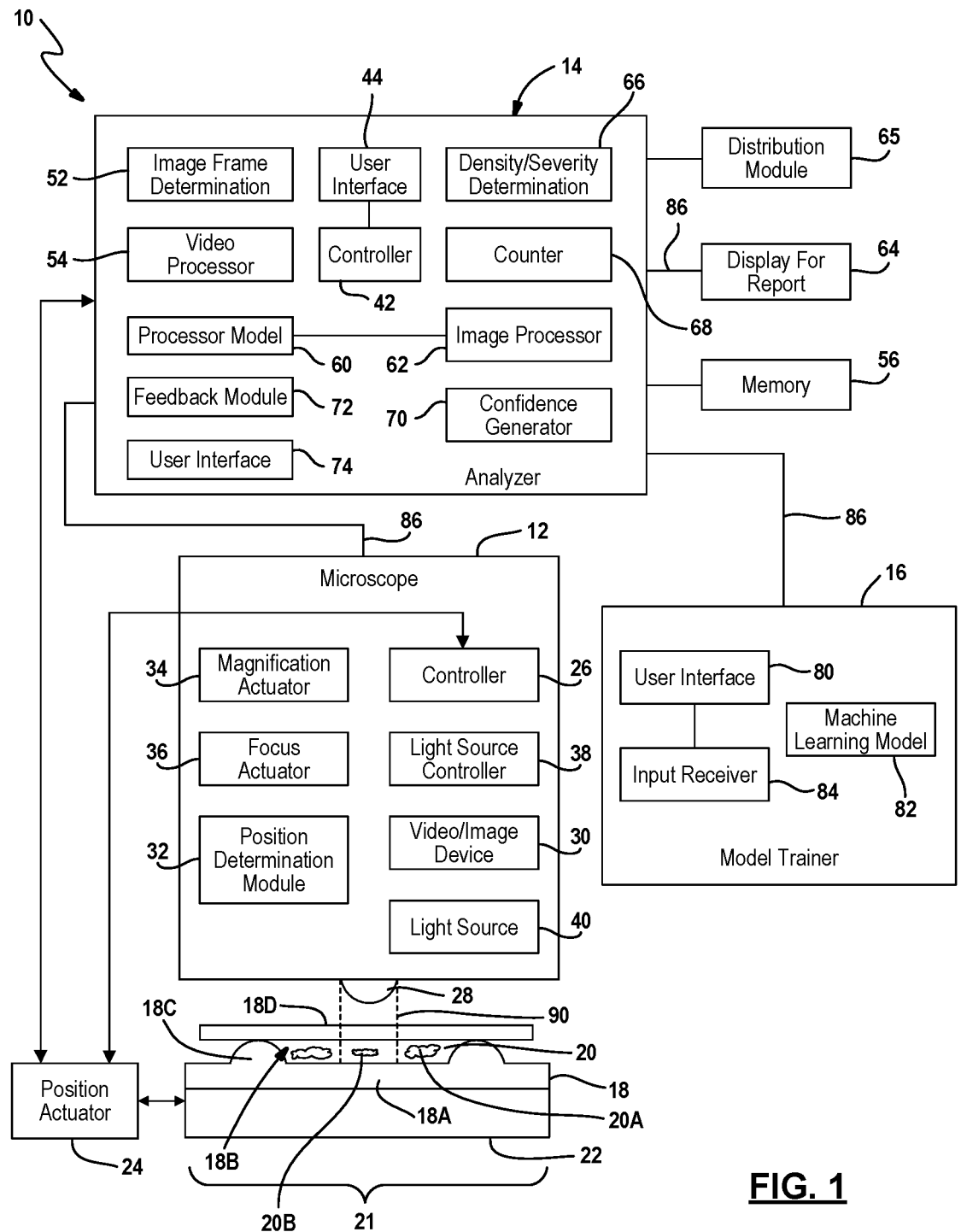
FIG. 1 is a block diagrammatic view of the system.

The following description is merely exemplary in nature and is not intended to limit the present disclosure, application, or uses. For purposes of clarity, the same reference numbers will be used in the drawings to identify similar elements. As used herein, the term module refers to an application specific integrated circuit (ASIC), an electronic circuit, a processor (shared, dedicated, or group) and memory that execute one or more software or firmware programs, a combinational logic circuit, and/or other suitable components that provide the described functionality. As used herein, the phrase at least one of A, B, and C should be construed to mean a logical (A or B or C), using a non-exclusive logical OR. It should be understood that steps within a method might be executed in different order without altering the principles of the present disclosure.

A system 10 for analyzing objects or structures in a bodily fluid sample such as blood is set forth. The system 10 has an image device such as a microscope 12 that is in communication with an analyzer 14. The analyzer 14 is in communication with a model trainer 16. In general, the microscope 12 is used to obtain images from a sample 20 within a sample holder 18A. The analyzer 14 is programmed to classify and analyze an image using a model generated by the model trainer 16. Although the system is illustrated as three separate components, one or more of the components 12, 14 and 16 may be incorporated into a single unit. The sample holder 18A has a well 18B formed thereon. The well 18B is surrounded by a wall 18C. The wall 18C may be various shapes including round or rectangular. A cover 18D is disposed directly adjacent to or rests on the top of the wall 18C. In one example, the volume of the well is completely filled with the bodily fluid sample 20. The bodily fluid may have objects such as biofilm 20A and pathogens 20B therein. Complete filling the well 18B allows the system to know the entire bodily fluid volume without further analysis. In other examples, the fluid volume may be obtained using the computer vision aspect of the analyzer.

Much of the focus of the examples set forth below is focused on the detection of biofilm. However, the identification of pathogens proximate the biofilm may provide diagnostic information as described in further detail below. In some examples, pathogens of interest may be nearby a biofilm, touching a biofilm, partially enclosed by a biofilm or completely encased within a biofilm. Resistivity to treatments may be hampered by the biofilms, especially the pathogens inside a biofilm. The position of the pathogen relative to the biofilm may provide an indication of the source of the biofilm as some pathogens create biofilm.

The sample holder 18A may be positioned on a sample positioner 21 such as a stager 22. The stager 22 is coupled to a position actuator 24. The position actuator 24 may move the stager 22 in an XY coordinate. However, the position actuator 24 may also move the stager 22 closer to or away from the body of the microscope 12 along the Z-axis to obtain the desired XYZ coordinates. As the stager 22 moves the sample holder 18A different fields of view are provided to the microscope 12 and different images for the different fields of view are obtained.

The microscope 12 has a controller 26 that is programmed to control various aspects of the system. The controller 26 is microprocessor-based and is programmed to perform various functions for obtaining images of the sample 20. The sample 20 may be imaged to obtain a plurality of images corresponding to the different fields of view on video by changing the relative position of the microscope 12 and the sample 20 in a predetermined manner. That is, the position of the microscope 12 may be changed or the position of the stager 22 may be changed or both.

The microscope 12 also includes a lens 28 that is used for obtaining the image or video. The lens 28 is coupled to the video/image device 30. The video/image device 30 may be a camera such as a digital camera or a digital video camera. A CCD or CMOS image sensor may also be used within the camera. The video/image device 30 may be a high or ultra-high resolution camera.

The controller 26 may also be used to control the position actuator 24, which may be a plurality of motors. The position actuator 24 is illustrated outside of the microscope 12 and may be coupled to the stager 22, the microscope 12, or both. The position actuator 24 may command the stager 22 to move in a calculated manner to obtain the proper number of images in predetermined positions. The position determination module 32 controls the sample 20 to predetermined positions relative to the microscope 12 and lens 28. The position determination module 32 may be part of or a separate module from the controller 26.

The controller 26 may also control or include a magnification actuator 34. The magnification actuator 34 may control the power of magnification of the microscope 12. Because the system 10 may be used for detecting biofilms of various stages of development and various objects such as pathogens within the bodily fluid, the magnification may be changed in order to make such detections of different size biofilm instances and other objects such as pathogens.

A focus actuator 36 is also in communication with the controller 26. The focus actuator 36 may automatically adjust the focus of the microscope. By adjusting the focus of the microscope, various three dimensional images or videos may be obtained. Focusing the lens 28 accommodate the various depths to allow clear mages to be taken.

A light source controller 38 may be used to control a light source 40. The light source 40 may be one or more different types of light sources having different spectrums with different wavelengths. Visual light or specific wavelengths of light may be generated by the light source 40. For example, ultraviolet light, infrared light or visible light may be generated. Specific wavelengths or combinations of light wavelengths may be used. More than one wavelength of light may be used for detecting specific objects and biofilms. That is, images of a particular sample may be made with more than one wavelength and classified in the analyzer 14.

The analyzer 14 also includes a controller 42. A user interface 44, such as touch screen keyboard or buttons, may be used for initiating functions, actuating various elements and entering various types of data. The analyzer 14 has an image frame determination module 52. The image frame determination module 52 may obtain image frames from a successive video frames or successive still frames. Should the video/image device 30 obtain video, various frames (still images) of video may be isolated for image classification. Base on a time code of the video, known frames may be removed from the time period when the sample was moving. Typically, thirty frames per second of video images are generated by a conventional video camera. However, other types of frame rates, including very high frame rates, may be used for classification.

A video processor 54 may receive the video from the video/image device 30 and the image frame determination module 52 may be used to capture various image frames. The captured images may be stored in a memory 56. The memory 56 may be within or outside of the analyzer 14.

An image processor 62 uses a processor model 60 that has been trained by the model trainer 16 to recognize images and segment images. Image segmentation is the process of partitioning an image into multiple segments. Image segmentation is typically used to locate objects and boundaries in images. The trained image processor 62 compares the image to the processor model 60 to obtain results. A results report is generated and sent to a display 64 for visual inspection and electronic distribution. The display 64 may be physically located at the analyzer 14 or may be located remotely through a network 86 and a distribution module 65 that may act as an interface for distributing the report through the network 86. An example of a report for conveying results of the classification are set forth below. The processor module may be trained to detect biofilms, pathogens and other objects. The processor model 62 may be trained with moving and non-moving objects. If only biofilms are being detected, moving objects may not be trained for recognition in the model.

The image processor 62 results or classifications include the location of the biofilms and the area and or volume and confidence score of the biofilm structure in each field of view (FOV) 90. Combinations of individual field of views 90 are added together to form the image of the sample for analysis. The FOV 90 and biofilm area information of the plurality of FOVs are used by the density/severity termination module 66 to calculate a total sample fluid volume in each FOV, determine the biofilm volume and biofilm count of each biofilm within each field of view, determine a total field of view biofilm volume and a total biofilm count by adding the plurality of biofilm volumes and biofilm counts for each field of view. The density/severity termination module 66 leverages the focus actuator 36 sample thickness calculation for the volume calculation as well as the counts obtained from the counter 68 module. That is, various images may be determined at various depths within the sample to ultimately determine the volume of the biofilm. The results from the density/severity termination module 66 are sent to the display 64 and distribution module 65 as a report in one example. A counter 68 may be used to count the number of FOVs analyzed and the number of biofilms located in a sample.

A confidence generator 70 may generate an indication of confidence in the determination of the presence of the biofilms, which is sent to the display 64 or the distribution module 65. Three measures of confidence generated may be generated: 1) an average confidence level and a variance of confidence level of biofilm found 2) weighted average and variance of the confidence level per biofilm found using summation of confidence level*volume for every biofilm found, 3) weighted average and variance confidence level per biofilm found using summation of confidence level*volume for every FOV.

A feedback module 72 may be used as part of the training of the image processor model 60. That is, feedback module 72, in conjunction with the user interface 44 may allow a user of the analyzer such as a doctor or other health care practitioner to confirm the results or disaffirm the results based on further testing. The results will be marked accordingly and leveraged during the by the input receiver 84 module of the model trainer 16. In this manner, the processor model 60 may be changed with feedback.

The model trainer 16 has a user interface 80 that is used to provide various data or perform various selections in the generation of the machine-learning module 82. An input receiver 84 is used for receiving inputs in the classification process. The inputs may include known specimens that have predetermined numbers and types of biofilms thereon or prior analyzed images with result marked by feedback module 72. The learning process will be described in greater detail below.

A network 86 may be used to communicate the processor model to the analyzer. The network 86 may be a computer network such as the Internet. In this manner, models may be communicated, updated, or new models may be provided from a central location to a number of analyzers 14.

The analyzer has a user interface 74 that may be used to enter various parameters such as a test identifier, a test or scan type or the like. Combinations of different types of user interfaces 74 may be used such as a bar code reader, a keyboard, a mouse, a touch screen or the like.

The analyzer 14 is configured to process imaging information by extracting features contained within the imaging information. The analyzer 14 is configured to extract at least one sample-informative feature and at least one candidate-informative feature. For some applications, the analyzer 14 is further configured to process the at least one sample-informative feature to obtain contextual information, and to process the at least one candidate-informative feature to obtain candidate data, as will be further detailed below.

Typically, the analyzer 14 is configured to classify and segment a likelihood of a candidate (i.e., a constituent element within the sample that exhibits characteristics that indicate that it may be a biofilm, and is therefore a candidate for being a biofilm) being a biofilm at least partially based upon the at least one candidate-informative feature. Further typically, the analyzer 14 is configured to classify/segment an image to determine a likelihood of the presence of biofilm in the bodily sample, by processing the at least one candidate-informative feature in combination with the at least one sample-informative feature. The image processor 62 performs this as will be described in further detail below.

More specifically, the analyzer 14 is programmed to classify/segment the likelihood of a candidate being a biofilm using classification and/or machine learning algorithms, e.g. support vector machines, neural networks, naive Bayes algorithms, etc. Examples of types of classification and/or machine learning algorithms used by the analyzer 14. For some applications, the computer analyzer 14 is trained, in advance of being used to analyze a bodily sample, using training images of bodily samples.

The analyzer 14 extracts from the one or more images, from the imaging information, and/or a portion thereof, one or more sample-informative features of the bodily sample that are indicative of contextual information related to the bodily sample. Typically, a plurality of sample-informative features are extracted. As used herein, "sample-informative features" include features of the bodily sample, which are not directed to a specific candidate and are usable to provide contextual information that can be used to determine the presence, likelihood of, or characteristics of biofilm in the sample, including, in some embodiments, the classification of specific candidates. By way of non-limiting examples, sample-informative features can include, for example, features related to non-candidate constituents in the sample, or features related to the quantity and/or distribution of cells of a given type in the sample. Features related to non-candidate constituents in the sample can include, for example, size-related properties of one or more non-candidates (including relative size as compared to either an expected size, or to an observed size of one or more other cells), movement of the object as compared to spaced apart in time images, shape-related properties of one or more non-candidates (including relative shape as compared to either an expected shape, or to an observed shape of one or more other elements). As used herein, an "expected" value (of, for example, size, shape, movement and/or intensity) is such value as may be known in advance of analyzing imaging information relating to a given sample.

For some applications, sample-informative features include features related to the distribution of candidates or biofilms within the sample or portions thereof. For example, if the number of candidates or biofilms found in a given image (or part of an image or a group of images covering a continuous portion of the sample) is significantly higher than the number of candidates or biofilms found in other parts of the same sample, this may indicate that the high concentration of candidates or biofilms found in one part of the sample might be a result of a local effect that should not affect the diagnosis of the sample. For example, a high concentration of candidates or biofilms (e.g. a high concentration of candidates overlapping red blood cells) in one part of the sample, but not in other parts, can be indicative of contamination, e.g., from a drop of blood from another sample that entered the sample under investigation.

In a pre-processing stage in order to determine, for example, whether some of the imaging information is of poor quality as measured by predetermined criteria (e.g., brightness, focus, etc.), in which case portions of the imaging information may be excluded from further processing in the image processor 62

The analyzer 14 extracts from the one or more images, from the imaging information, or/and from a portion thereof, one or more candidate-informative features associated with one or more identified candidates. Typically, for each candidate, a plurality of candidate-informative features are extracted. As used herein, "candidate-informative features"

include features of the candidate useable to provide information for determining the likelihood of the given candidate being a biofilm.

By way of non-limiting example, candidate-informative features can include features related to: a size of a candidate, a shape of a candidate, a motion of a candidate (based, for example, on a comparison of at least two at least partially overlapping images captured in sequence), and/or an intensity of a candidate.

For some applications, candidate-informative features include a relative location of a candidate with respect to other sample constituents (e.g., a red blood cell). Alternatively or additionally, candidate-informative features include a property of a cell (e.g. red blood cell) that at least partially overlaps with or is enclosed within the candidate biofilm (and, optionally, also the amount of overlap), such as a size or shape of cell overlapping the candidate. For some applications, features related to size and shape of a cell overlapping the candidate include a relative size and relative shape of the overlapping cell as compared to an expected size or expected shape. As used herein, a cell is considered to overlap with a candidate at least partially if, in the imaging information, at least a portion of the cell appears to be co-located with at least a portion of the candidate (e.g., at least 20 percent or at least 25 percent of the candidate).

For some applications, the imaging information or a portion thereof is processed for candidate-informative feature extraction at least partly in a pre-processing stage. In certain embodiments, the pre-processing stage can include extracting sample-informative features to obtain contextual information, and determining the imaging information, which is used to extract candidate-informative features in accordance with the obtained contextual information. For some applications, the portion of the imaging information, which is used for extracting candidate-informative features, and the portion of the imaging information, which is used for extracting sample-informative features partially or completely, overlaps. Typically, based upon the candidate-informative feature(s) in combination with the sample-informative feature(s), the image processor 62 classifies a likelihood of the bodily sample having biofilm structures.

For some applications, once at least some candidate-informative features are extracted, in the image processor 62 and the confidence generator 70 classifies the likelihoods of respective candidates being biofilms, in accordance with the candidate data obtained for each respective candidate. As used herein, the term "likelihood of being a biofilm" should be expansively construed to cover either a binary determination (e.g., either a biofilm or a non-biofilm) or a scalar determination (e.g., a number, the value of which reflects the estimated likelihood that the given candidate is a biofilm). In certain examples, image classifier 62 classifies the likelihoods of respective candidates being biofilms using the extracted sample-informative features in combination with the candidate-informative features.

For some applications, the processor 62 generates an output to the user (e.g., on the display device 64) indicating whether or not the sample contains biofilm, and indicating a classification of the infection. The classification of an infection may take into consideration the pathogens or other objects proximate the biofilm. For some applications, the processor 62 generates an output signal indicating that the presence of an infection within the bodily sample could not be determined with a sufficient degree of reliability, indicating that a portion of the sample should be re-imaged, and/or indicating that a portion of the sample should be re-imaged using different settings (e.g., using different lighting, using a different stain, using a different or new sample preparation method, and/or using different microscope settings). For some applications, in response to determining that the presence of an infection within the bodily sample could not be determined with a sufficient degree of reliability.

It is noted that, for some applications, sample-informative features are not necessarily derived directly from the images. For example, sample-informative features may include statistical or other information regarding the candidates and/or other entities within the sample, and/or general characteristics of the sample. In general, the scope of the present application includes analyzing a sample on two levels, first on a candidate-by-candidate level, and then on a more general level that is indicative of characteristics of the sample as a whole.

For some applications, based upon candidate-level features, two or more sample-informative features related to the bodily sample are extracted, and a characteristic of the bodily sample is determined, by processing the two or more sample-informative features. Typically, at least some of the candidates are biofilm candidates, and candidate-informative features relating to the biofilm candidates are extracted. For some applications, the sample-informative features include a number of biofilm candidates in the sample, type of biofilm candidates in the sample, a probability of candidates being biofilms, number of candidates that have a probability of being a biofilm that exceeds a threshold, number of candidates that have a probability of being a given type of biofilm that exceeds a threshold.

Figure 2:
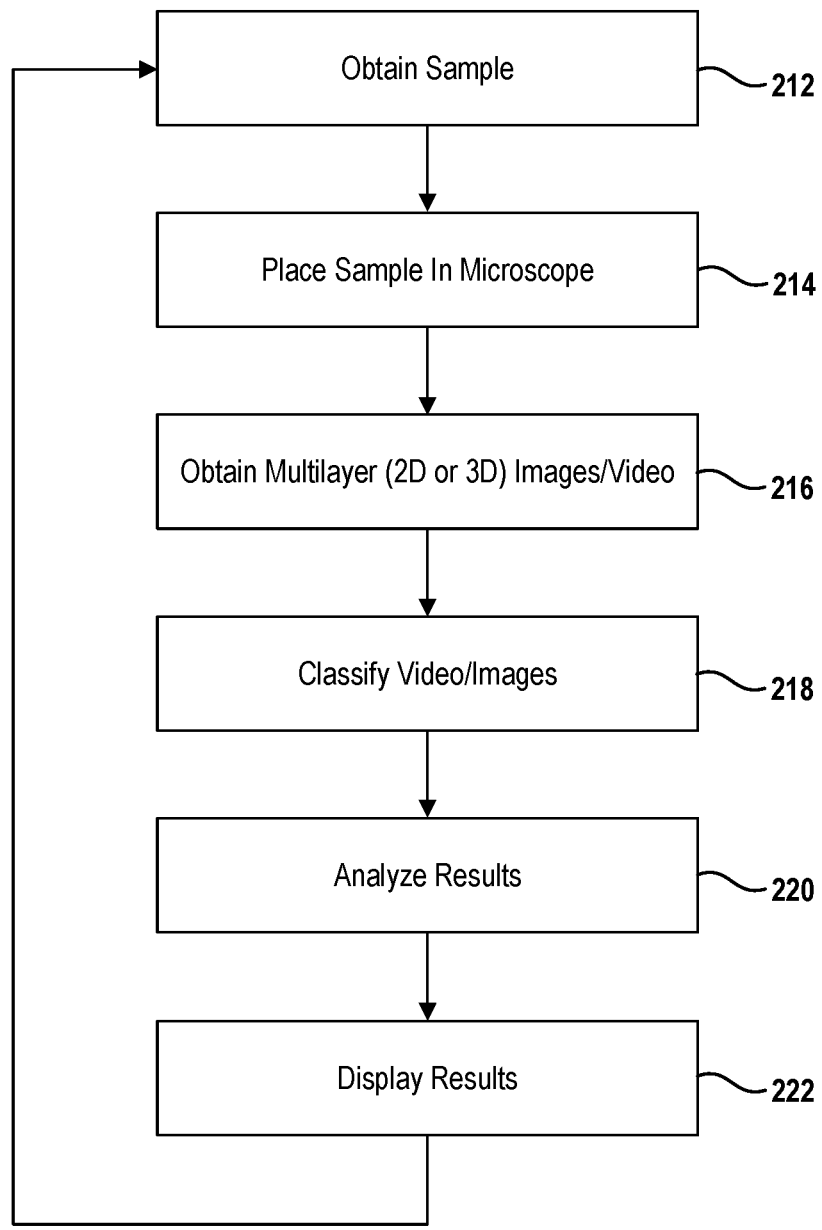
FIG. 2 is a flow chart of a method for detecting a biofilm.

Referring now to FIG. 2, a high-level method of operating the system is set forth.

In step 212, a sample of bodily fluid for analysis is obtained as described below. In step 214, the sample is placed near the microscope or other image determination device. As mentioned above a well with a predetermined volume may be used, with or without a cover.

In step 216, a multi-layer or three dimensional video or images of structures or objects are obtained for a scanning area. The combination of the plurality of images may also be referred to as a combined image. The combined image may essentially be a stitched together image representing the entire volume of the sample in the scanning area. In step 218, the objects or structures in the video or images are classified. All the objects or structures may be classified individually as a biofilm or not a biofilm. However, movement of structures or objects may be terminated so that any moving object does not need to be classified because biofilms are non-moving. That is, moving object may be classified as non-biofilm and the remaining stationary objects or structures may then be classified. Biofilms are large relative to some objects or structures in fluid samples. Size may be another filter. Object smaller than a predetermined are may also be classified as not being a biofilm. The results are analyzed in step 220 and results are displayed and reported in step 222. The results displayed may correspond to the severity or density of the biofilms within the bodily fluid or other indications of the presence of a biofilms. Details of the display and a report are also set forth below.

Figure 3:
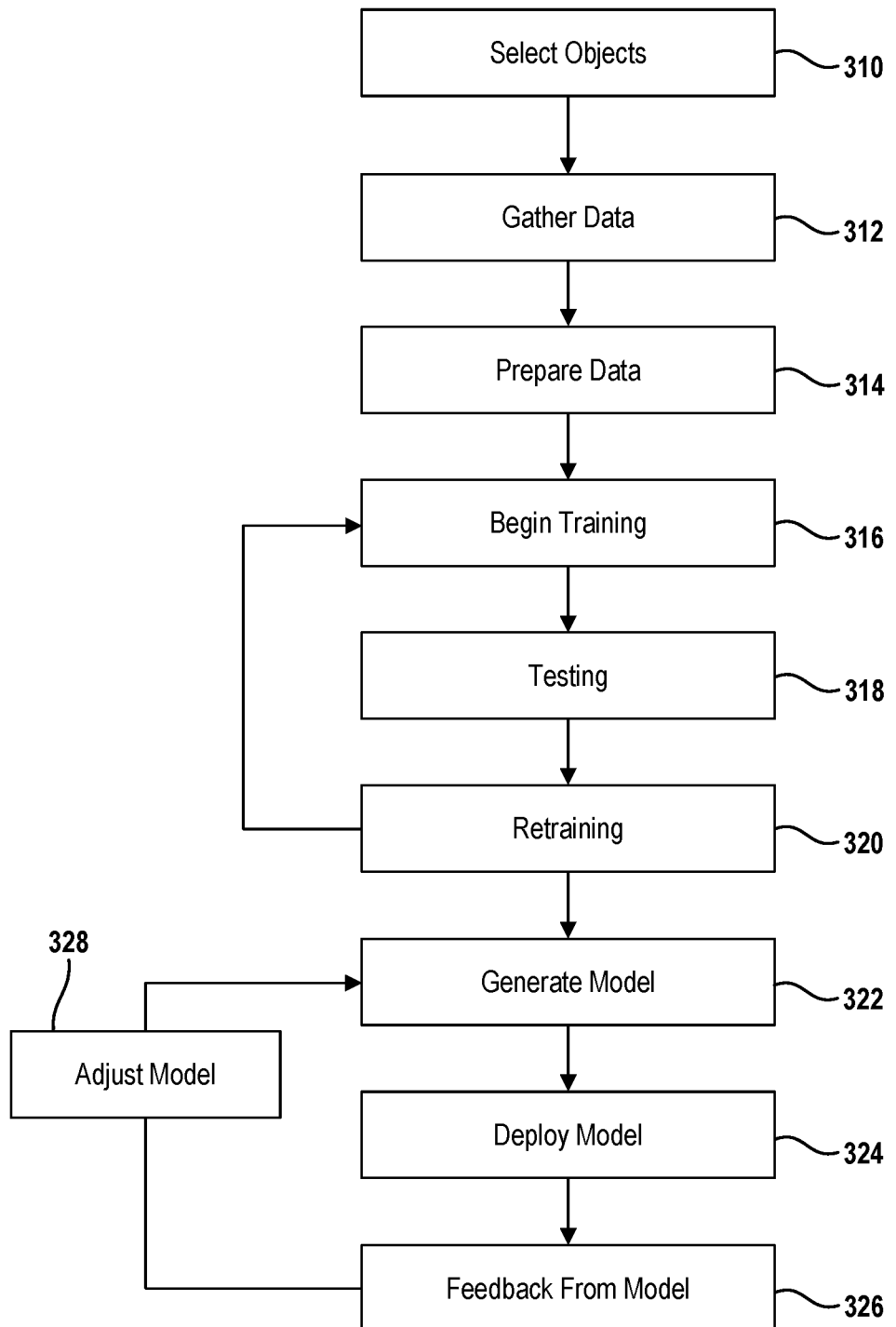
FIG. 3 is a flow chart of a method for training a machine-learning model.

Referring now to FIG. 3, a method for training a processor is set forth. In step 310, objects are selected for training of the image processor. Organic structures, objects or bacteria that are visible under a microscope may be used. Ultimately, the selected objects are the objects that are desired to be identified by the analyzing system. In step 312, data is gathered for training of the image processor. In one constructed example, it was desirable to identify biofilm for the detection of Lyme disease. However, in the training process, symplasts were used for training. The symplasts images were "negative" relative to the model. The symplasts are used in contrast to spirochete and biofilm. Symplasts were to not be identified as biofilms. This is described in more detail below.

In step 314, the data was prepared. The data for the three different categories used in the present example is formatted for proper processing by the model trainer. The syntax such as human readable form is changed to a computer-readable format. Missing, incomplete or corrupted data is also purged from the datasets. The data may be organized for a logical training process. In the present example, videos of biofilms and symplasts were used. Still images were obtained from the video. Some of the images were set aside for later use to test the model.

In step 316, the training process is started. A supervised learning approach for entering data may be used. That is, the model trainer may be provided with an image and mark the biofilm found within the image. In this manner, the common characteristics of each different type of biofilm may be determined by the model trainer. Of course, a relative small number to thousands of samples may be provided to a system depending upon the complexity of the biofilms. The factors for the amount of training data required include, but are not limited to, the quality of the training data, the desired sensitivity of the model, the number of categories and the difficulty level of the tasks. In step 318, the model may be tested using some of the data set aside as previously described above. The set aside data is known data and thus the model may be tested to see how it performs. The testing data is not used in the training of the model. Typically, a considerable amount of testing data may be set aside for testing purposes. For example, about 20% to about 30% of data may be reserved for testing rather than training. During testing, when the model is not performing adequately, the system may be retrained in the retraining step 320. Retraining takes place by performing the training step 316 and the testing step 318 repeatedly until adequate results are provided. It is desired to prevent "overfitting" of the data. That is, if too much training is provided, a danger of false negatives may also be obtained.

After each training iteration, the testing step 318 is performed and the results are compared to the previous training iterations.

In step 322, the model is ultimately generated based on the training and the retraining steps provided above. In step 324, the model may be deployed. That is, once the processor model is trained to the desired state of performance, the model may be communicated to the analyzer and used in real world classification. In a health care setting, the model trainer 16 may be located at one location and the image processor may be located at another location such as within a doctor's office. Updated processor data may be communicated through the network 86 illustrated in FIG. 1.

In step 326, once the model has been provided in a clinical type setting, feedback may be obtained. Feedback may be obtained for the model based upon use and further testing using a different type of system. In step 326, feedback may be provided based upon additional testing. The feedback may be used to adjust the model in step 328. That is, the adjustment of the model may be performed and taken into consideration in step 322.

The model is adapted and benefits through multiple training using data as well as benefitting from feedback. The feedback may also be communicated back to the model trainer through the network 86 to make the model for future applications better. Feedback may be provided to the model trainer through images and data corresponding to the images such as positive or negative results. This allows the image processor to train and retrain itself in real time using the feedback and better informed calculations. Continuous refinements allow better results to be obtained in the future.

Figure 4:
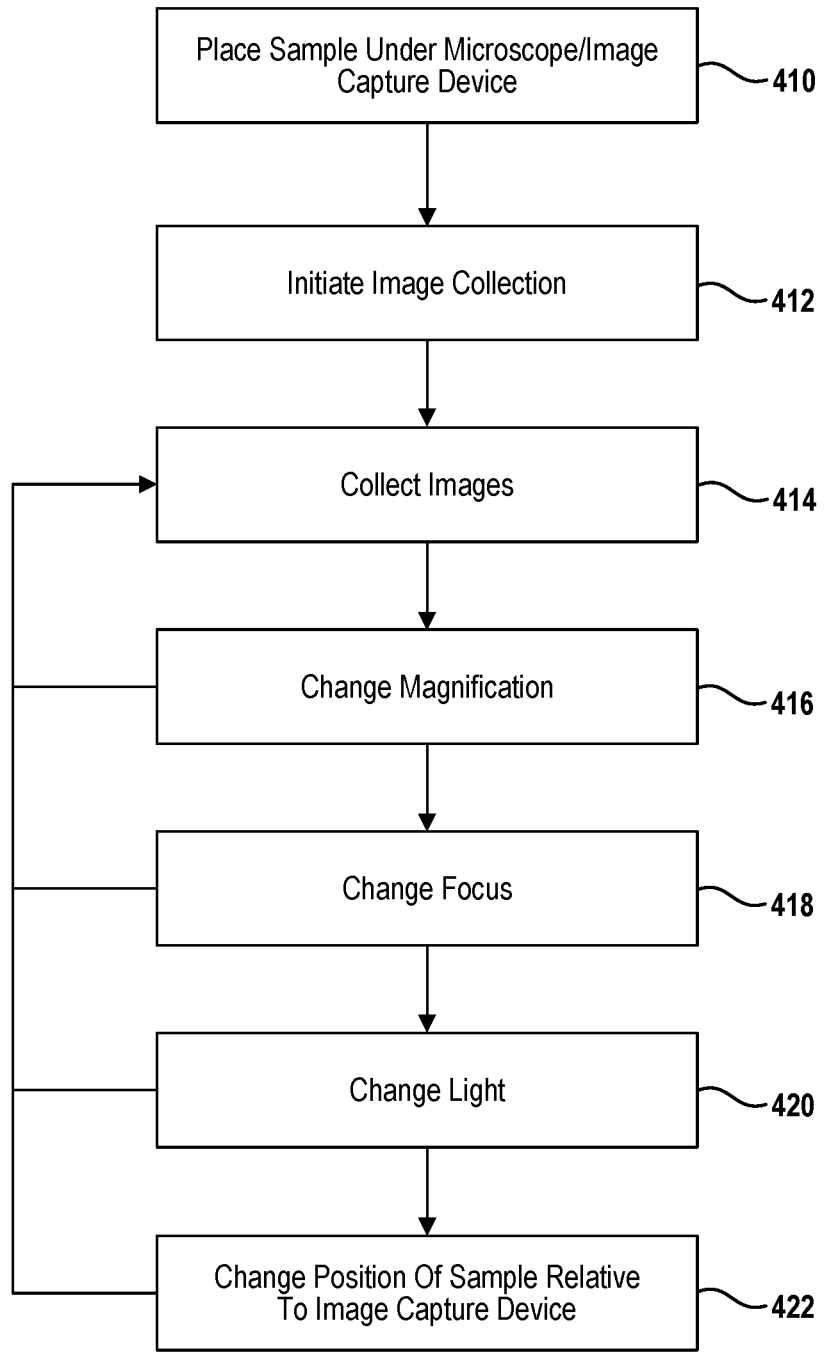
FIG. 4 is a flow chart of a method for obtaining images.

Referring now to FIG. 4, in step 410, a sample is placed within view of the microscope or image capture device. As mentioned above, the microscope 12 or image capture device may have a stager 22 that moves in various planar directions relative to the lens 28. This allows for the calculation of thickness of the sample and the density of the biofilms being determined for a predetermined chamber sample volume. In detail analysis mode, for each FOV of the sample holder, the stager will move the sample at predetermined z-axis depth positions and a video recording will be capture at each position. When a biofilm structure is found, the image classification/segmentation system will determine volume by summation of the 2D area of each biofilm structure in all FOV z-axis depth positions*total z-axis distance traveled. In step 412, image collection is initiated. The initiation of the image collection may be performed at the analyzer 14 described above. The user interface 44 of the analyzer may be used to initiate the process and select the biofilm or biofilms desired to be protected. The image collection may be initiated by obtaining a video of a predetermined sample and the collecting images in step 414 from the video. Of course, still images may be obtained directly rather than from a video.

In step 416, the magnification of the microscope may be varied depending upon the desired size of the biofilm. If more than one biofilm is selected, the magnification may change during the process. Multiple images may be collected in step 414 by varying the various perimeters of the microscope or image collection device. For example, in step 416, the magnification may be changed multiple times during obtaining of images to detect various sizes of biofilms. In step 418, the focus may be changed to focus at various levels or various positions within a sample. In step 420, the lighting may be changed. Multiple types of light sources, as described above, may be used. Images may be taken from a sample using more than one wavelength of light. That is, an image may be taken with one wavelength and a second image with the same settings at the same location may be taken with a different wavelength. The proper wavelength may change depending on the particular biofilm.

In step 422, the position of the sample relative to the image capture device is changed. The position actuator 24 described in FIG. 1 may be used to change the position of the stager 22 relative to the lens 28 of the microscope or imaging device. Images may be taken from various parts of the sample including higher or lower depths and various XY positions. This allows a three-dimensional set of images to be obtained. Again, the images may be obtained from a video and the video taken while the position actuator 24 moves the stager 22.

Figures 5, 6:
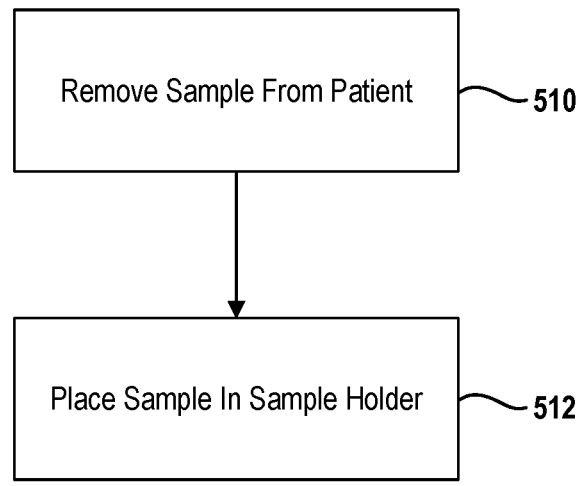
FIG. 5 is a flow chart of a method for obtaining a sample.
FIG. 6 is a screen display for the analyzer.

Referring now to FIG. 5, a method for obtaining a sample is set forth. In step 510, a sample is removed from the patient. The sample may be removed by a needle or withdrawing a blood from the patient. If other bodily fluids are used, other methods for obtaining the bodily fluids may be used. In step 512, the sample is placed in a sample holder. The sample holder may, for example, be a sample holder or well type device. As mentioned above a cover may cover the well during image analysis. For certain biofilms, time may be critical due to breaking down of the objects and thus the analyzing may be performed within minutes of obtaining the sample. The cover may prevent contact with the microscope and reduce the disturbing the sample. The analyzer may be located in a lab or doctor's office so that easy access to a free sample may be provided.

Referring now to FIG. 6, a report 600 is generated by the analyzer 14. The report may then be displayed and sent to the display 64 for display at the analyzer or communicated to the distribution module 65 where the report may be displayed immediately or at a later convenient time. The report may also be communicated to and stored in the memory 56. The report 600 is simplified and provides indicators corresponding to the presence, amounts, and of severity of biofilm. The confidence in such values is also provided. In this example, for the sample analyzed, the report containing a number of analysis measurements and calculations that for the indicators. A greater number or lesser number of calculations and measurements may be used. The display 64 has a sample identifier 610 that is a unique identifier for the sample analyzed. Number of FOVs analyzed 612 represents the number of FOVs analyzed to form the sample area. One indicator is a biofilm occurrence density ratio 614 calculated as a number of biofilm occurrences divided by the total volume of the overall fields of view. Another indicator is a biofilm density ratio 616 calculated as a total volume of biofilms divided by the total volume of the field of views. Another indicator is an average confidence score 618 is calculated as sum of the individual biofilm confidence scores divided by the biofilm occurrences. Yet another indicator is biofilm volume weighted confidence score 620 calculated as a (sum of the biofilm confidence scores*total volume of biofilm)/biofilm occurrences. Another indicator is the field of view (FOV) volume weighted confidence score 622 calculated as (sum of the biofilm confidence scores*total volume of the field of views)/biofilm occurrences. For each of the 616-622 a variance may be provided as well. A first variance is generated based upon the biofilm density ratio. A second variance is generated relative to the average confidence score. A third variance is generated based on the biofilm volume weighted confidence score. A fourth variance is determined based upon the field of view volume weighted confidence score.

Figure 7:
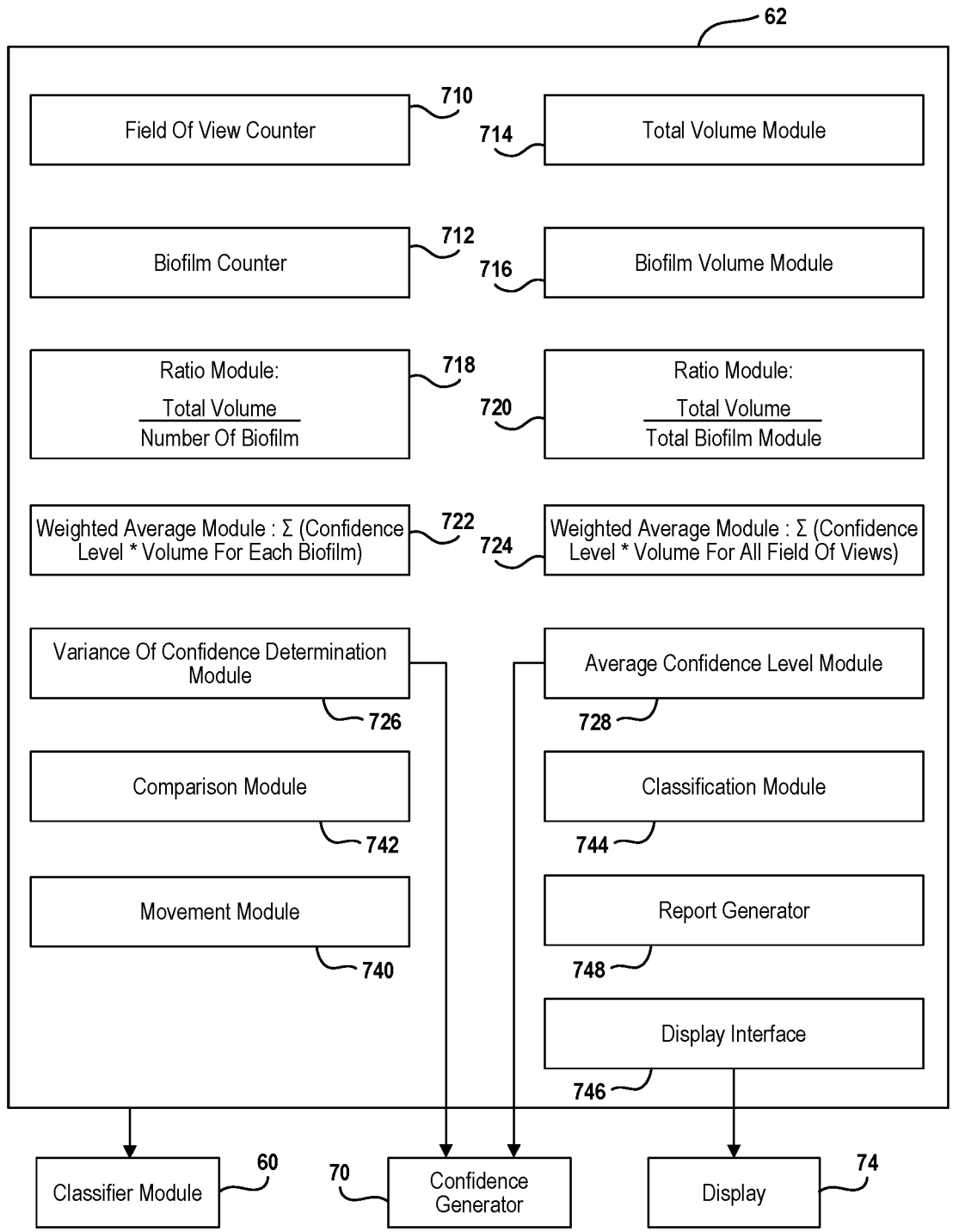
FIG. 7 is a schematic view of the image processor for classifying and segmenting images.

Referring now to FIG. 7, a portion of the system of FIG. 1 is illustrated in further detail. In this example, the image processor 62 has a plurality of modules that corresponds to identifying a biofilm as distinguished from other objects within in a bodily fluid sample. In this example, a processor module 60 that has plurality of images of various objects such as biofilms is provided.

The image processor 62 has a field of view counter that counts the number of fields of view during the scanning process. The field of view counter 710 may be part of the counter 68 illustrated in FIG. 1. A biofilm counter 712 is used to count the number of biofilms determined within a scan. The biofilm counter 712 counts the biofilm detected in each field of review as well as providing an overall biofilm count. A total volume modular 714 is used to provide a total volume for the sample. The total volume for the sample may be predetermined in that a sample holder with a known well volume may be used in the system. The total volume module may also perform a calibration to determine a volume of a well and thus a sample.

The optional calibration of the sample holder having a thickness (z depth) may be performed. Upon first setting up the microscope, the microscope may be calibrated by measuring the distance from the lens to the sample holder at four corners of the sample holder. The sample holder will have some kind of marking on each of the four corners that the microscope will be able to focus on. This gives a reference point and distance. Since the distance between the lens and staging area where the sample holder is placed may differ each microscope, the one-time calibration may be necessary.

If a new sample holder type is placed on the stager 22, or other related instrumentation is changed, the distance between the sample holder 18A and the cover 18D may need to be calibrated. This may need to be calibrated each time a new sample holder is placed because the sample holder and/or cover may vary (albeit the distance may be so insignificant, like a couple of microns, that this second calibration may not be necessary). The second calibration provides an indication of the thickness of the sample being between the sample holder and the cover. The cover may have markings on the four corners at approximately the same areas as the sample holder so that when the coverslip is placed directly over top the sample holder, the markings will line up.

The image processor 62 may also include a biofilm volume module 716. The biofilm volume module generates a biofilm volume for each of the biofilms detected within the field of view. The biofilm volume module 716 may also sum together the volume of biofilms within the entire field of view to obtain the total biofilm volume.

From the determinations from the elements 710-716, one or more indicators may be generated and displayed. A ratio module 718 may be used to generate a ratio of the number of biofilms occurring in the sum total volume of all the fields of view (biofilm occurrence density ratio). Another ratio module may be used to generate a biofilm density ratio corresponding to a total biofilm volume relative to the sum total volume of all the fields of view.

A weighted average module 722 may be used to generate the biofilm weighted confidence score which is the (sum of the confidence scores*the total volume of biofilm) divided by the number of biofilm occurrences. Another weighted average module 724 may be used to generate a field of view weighted confidence score which is the (sum of the biofilm confidence scores*the volume for all the field of views) divided by the number of biofilm occurrences.

A variance of confidence determination module 726 may be used to determine the variance of the confidences determined at the confidence generator 70. This may be an average confidence score of the sum of the biofilm confidence score divided by the number of biofilm occurrences. The confidence generator 70 determines the confidence of the different measurements or determinations described above. Biofilm volume module 716 may also determine the area of the biofilms. That is, the biofilm volume module 716 may determine the area of the biofilm in two dimensions relative to an image. The overall volume of the biofilms may be summed together in the biofilm volume module 716. As mentioned above, various numbers of scans may be performed at different depths. Thus, scans may be used to determine the areas at the different depths. By extrapolation, the volumes may thus be determined by taking into consideration the areas of the biofilms and the depths between the different layers.

A movement module 740 may be used to determine movement of objects within successive images. The movement module 740 is described in further detail below. The movement module 740 can detect moving objects versus stationary objects. Biofilms are stationary and other types of objects may be stationary such as a symplast. Red blood cells and macrophages are examples of moving objects. In general, the super position of successive images may be indicated by a color and thus colored objects may be removed from consideration prior to classification based upon computer vision.

A comparison module 742 may compare the objects to different types of images using machine learning. Based upon the classifier modules 60, the comparison module 742 is used to distinguish biofilms from other objects. Pathogens and proximity to a biofilm may be identified as well.

A classification module 744 is used to classify and segment the amount of infection based upon the comparison of the biofilm area to the FOV area. That is, the overall biofilm area may be divided by the overall FOV area to determine a percentage or ratio. That is, the amount of area versus the FOV area may be used by the classification module 744 to determine whether the sample has a sufficient amount of biofilm to be classified.

Upon completion of the analysis, a display interface 746 and a report generator 748 communicate with the display 64 and optionally to the distribution module 65. The display interface 746 is used to generate a display signal, which may be an audible signal or a visual signal, that provides an indicator for the presence of biofilm in the particular sample. For example, the display 64 may generate "THE SAMPLE HAS BIOFILM DETECTED". The display may also generated a display that states "No Biofilm Detected." Of course, other types of biofilms may be determined and a list of the types of biofilms as well as the concentrations or volumes of biofilms within the FOV may be determined. Of course, the various indicators determined may be stored within the memory 56 for later use and comparison.

Referring now to FIGS. 8-11, the movement module 740 of FIG. 7 may be used for determining the movement of objects within a fluid sample to distinguish the moving objects from non-moving biofilms within a sample. More specifically in FIG. 8, the detection of movement is determined by successive images 810A, 810B and 810C that are illustrated as the rectangles. As will be described in more detail below, the images 810A, 810B, and 810C are taken in sequence a predetermined time period apart. The time period between the images may vary and depends upon the biofilm, object or organism to be detected. In the present example, the images are colorized in succession. The color of each succession may vary. By way of example, an image from timestamp 0 min 5 second, a second image from timestamp 0 min 15 second, and a third image from timestamp 0 min 25 second. The time interval between images may be adjusted as needed and may even include flexible time intervals such as a 5 second time interval between images 1 and 2 and an 8 second time interval between images 2 and 3. There can also be overlap between groups of three images, for example, one group of three images includes an image from timestamp 0 min 5 second, a second image from timestamp 0 min 15 second, and a third image at timestamp 0 min 25 second. Then, a second group of three images can be comprised of an image from timestamp 0 min 6 second, a second image from timestamp 0 min 16 second, and a third image at timestamp 0 min 26 second.

In the present example, the first image 810A corresponds to a red image. That is, the object within the image is colored red. In the second image 810B, the object is colored green. In the third image 810C, the object is colored blue. The composite image corresponds to the combined layered images with colorization to denote where sequential changes in pixels have occurred between the images. That is, the three successive images are combined digitally and thus movement can be detected by detecting the colors. In the present example, an area or object that has changed position from the first image 810A to the second image 810B and the second image to the third image 810C is red and corresponds to the red area 814A. An object within the area 814B shows a combination of image from the green colorizations to form yellow. That is the object was in the same place when the first image 810A and the second image 810B were taken but moved before the third image 810C was taken. Areas 814C are green and show that the object was not present in the position in the first image 810A but was at the position in the second image 810B but moved before the third image 810C and thus the object is green. Areas when green and blue are combined are cyan in the area 814D. In the cyan area 814D, the image was not present at the position in the first image 810A but stayed in the position in the second image 810B and 810C. Objects that are blue in the blue area 814E where not present in the first two images 810A and 810B but was present at the position in the last image 810C. When the three areas are combined, movement is not present, as set forth in 814F. In 814F, if the object does not move in the three successive images, three colors are overlapped and thus a white portion of the object is found. Examples will be described in more detail below. By determining the color, the amount of movement and thus the type of biofilm may be determined. Not only will movement and the velocity or change of movement be determined, but the type of movement and the direction of movement may also be determined. Various types of pathogens move in different ways and thus these different ways may be determined by the sample-informative features and the candidate informative features as described in more detail below. Because biofilms are stationary, they may be distinguished from moving objects such as a pathogen. When the object moves in the last images, cyan is displayed as the color.

Figure 9A:
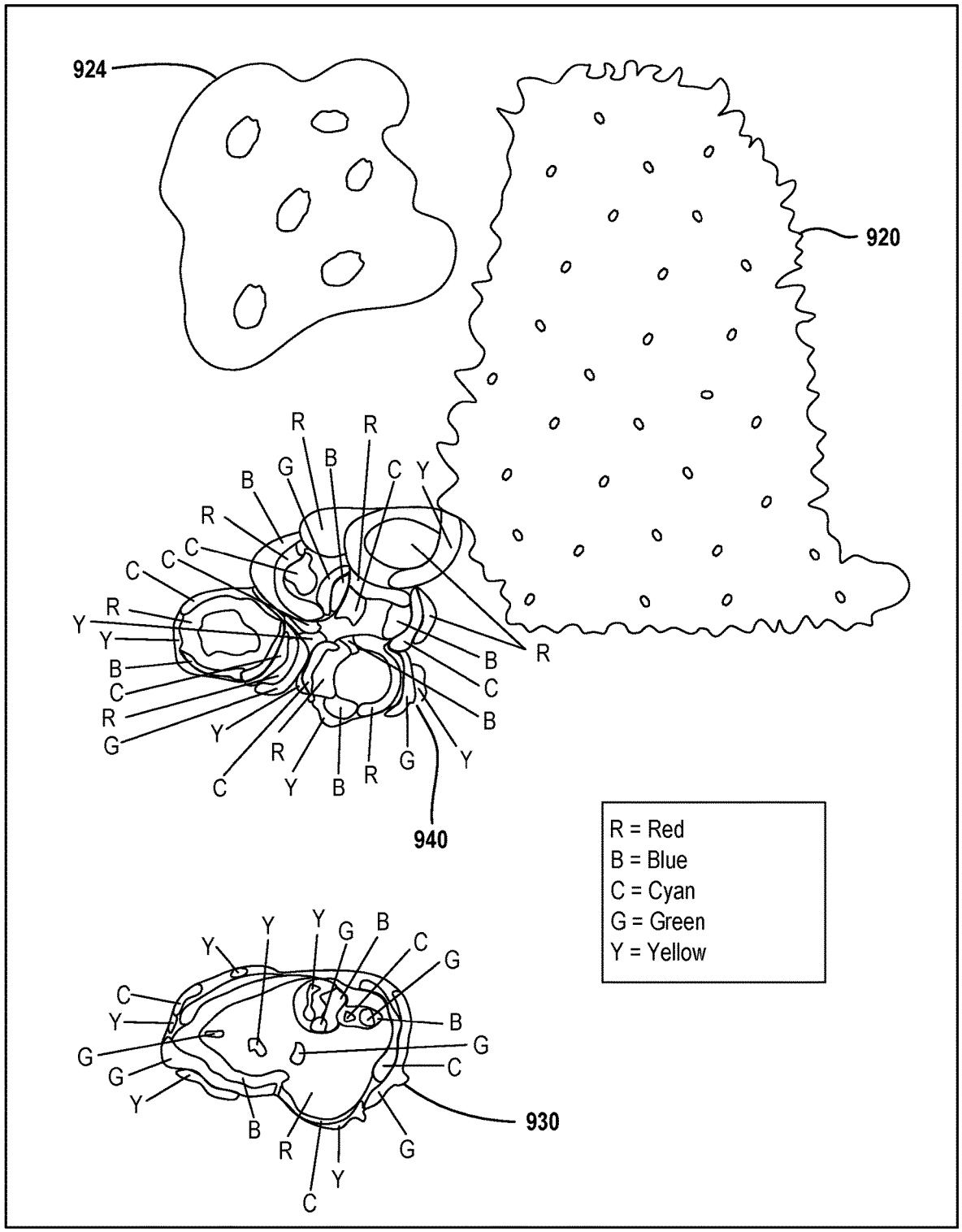
FIG. 9A is a composite image of an object formed from a plurality of colored images.

Referring now to FIG. 9A, one example of objects in a composite image 910 is set forth. The composite image 910 includes a biofilm 920, a symplast 924, a macrophage 930 and a plurality of red blood cells 940. The composite image 910 is a composite in several aspects. The composite image 910 combines a field of view from three (3) successive views in time. The successive views may be a predetermined amount of time such as a quarter of a second to 15 seconds apart.

The biofilm 920 has no colorized portions because the biofilm 920 does not move. The symplast 924 also does not have colorized portions because a symplast does not move.

The macrophage 930 and the red blood cells 940 have colorized portions in red, blue, cyan, yellow and green. As compared to FIG. 8, the colored regions indicate movement. Cyan indicates that movement between the first and second images while the third image the object remained in place. White portions indicate the object has not moved. The green position indicates movement between the second image and third image.

Figure 9B:
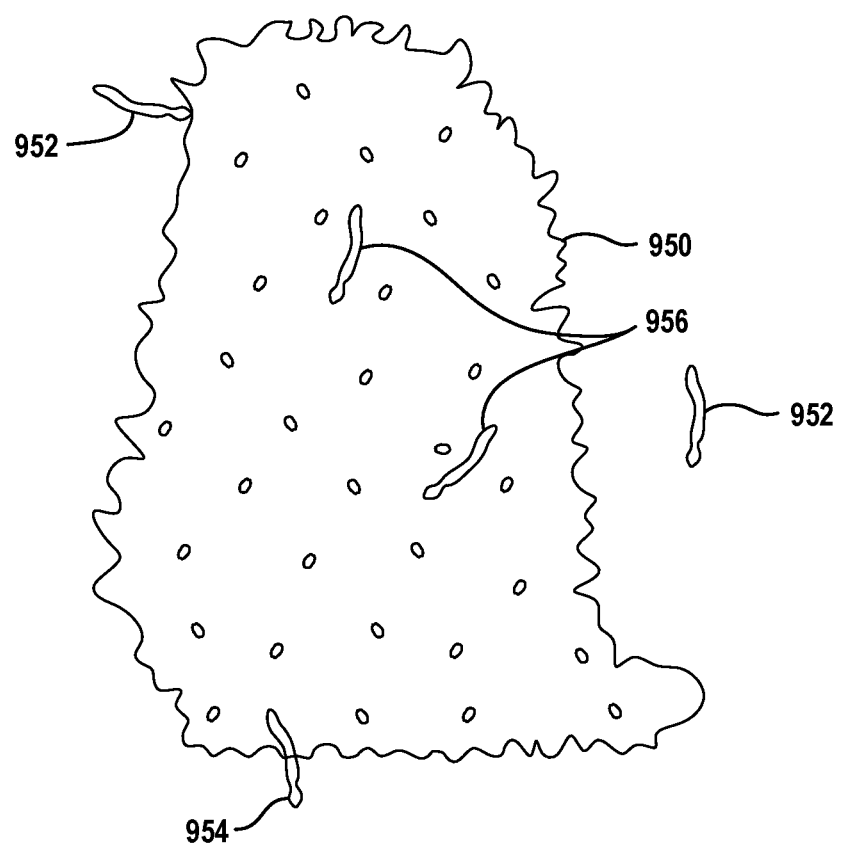
FIG. 9B is an image of a biofilm proximate pathogen, spirochetes in this example.

Referring now to FIG. 9B, another example of a biofilm 950 is set forth. In this example, a pathogen such as spirochete is provided in many locations. A first spirochete 952 is disposed adjacent to but separated from the biofilm 950. A second spirochete 954 is illustrated touching but not included in the biofilm 950. A third spirochete 954 is disposed partially and partially powered of the biofilm 950. Two spirochetes 956 are disposed entirely within the biofilm 950. The spirochetes 956 may be particularly difficult to treat with drugs. Although movement is not illustrated in FIG. 9B, the spirochete may move in a similar manner and therefore be detectable using colorization described above in FIG. 9A.

Figure 8:
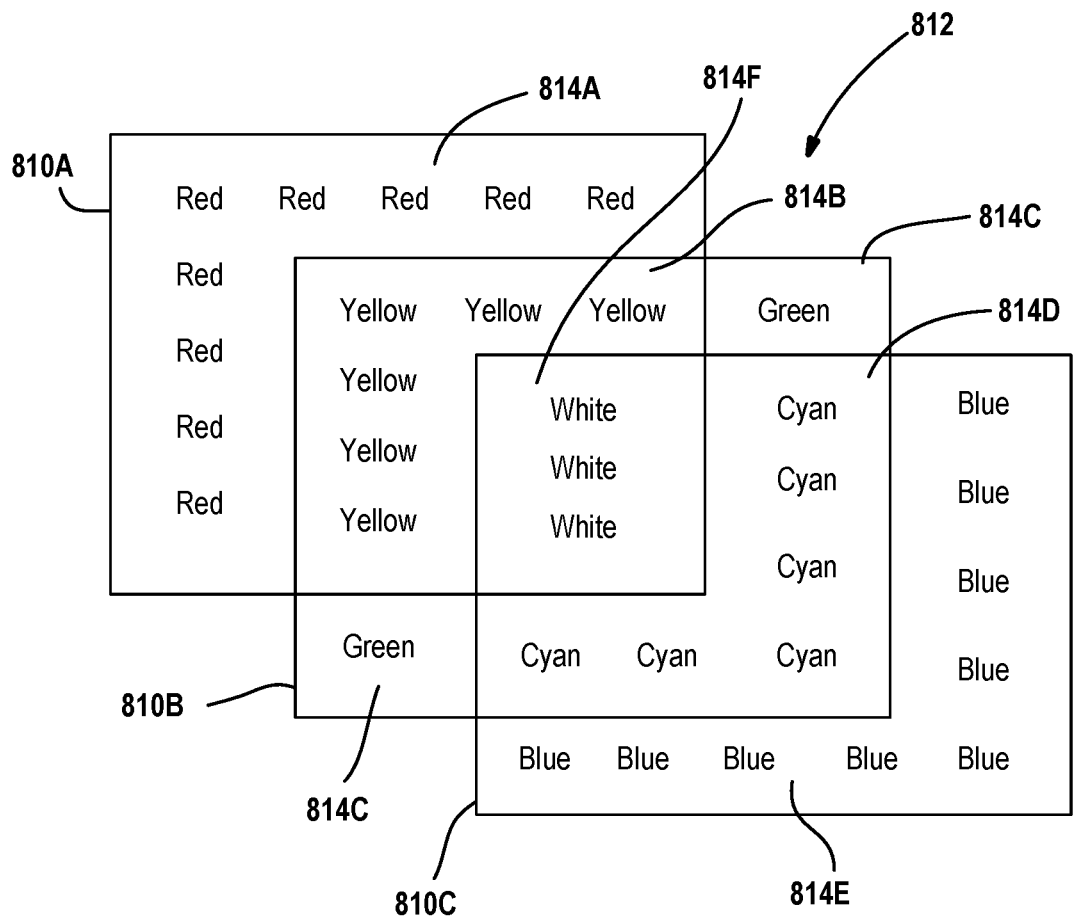
FIG. 8 shows a sequential view of different images and the overlap of colors between the images.
Figure 10:
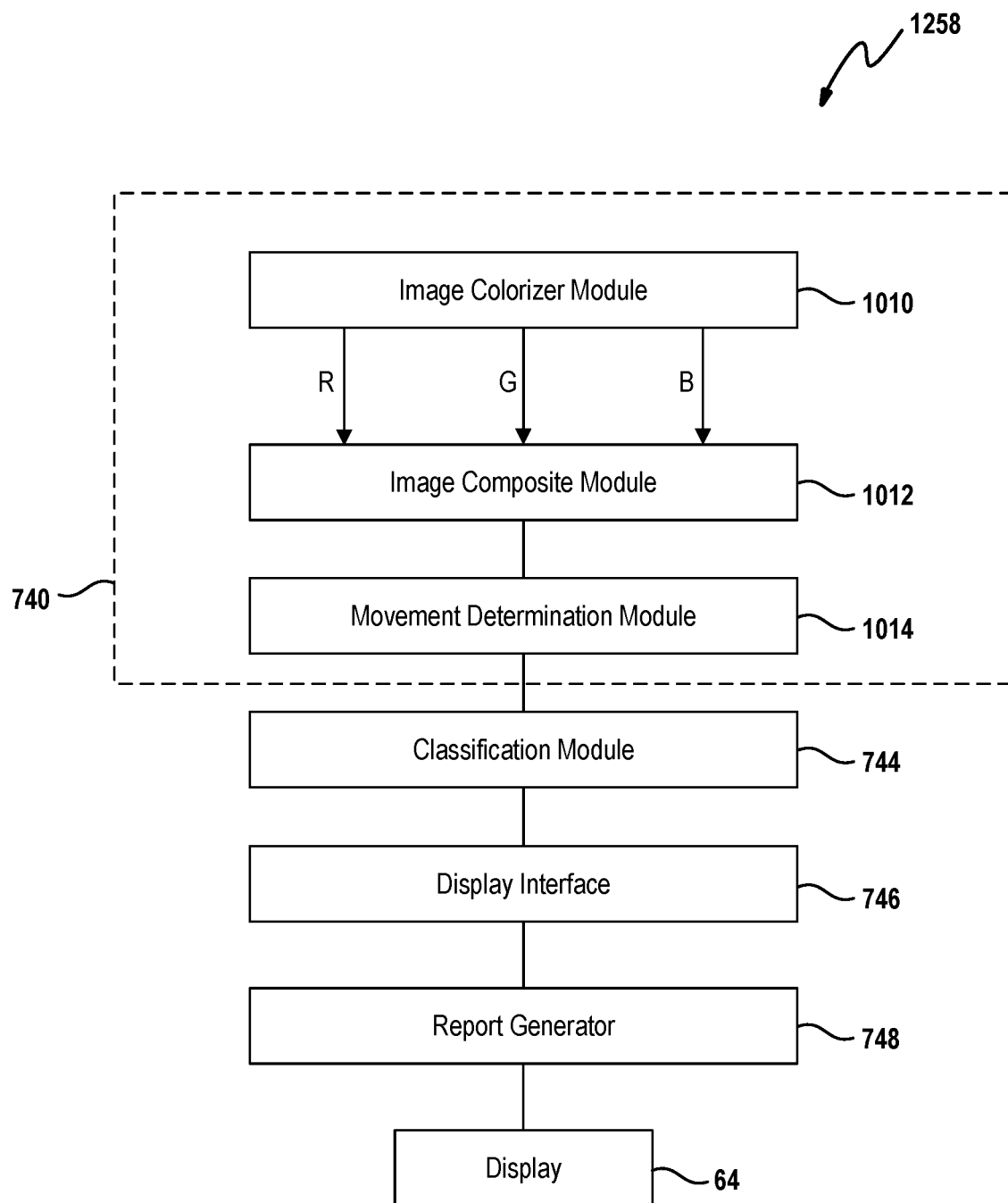
FIG. 10 is a schematic view of the image processor 62 for generating and classifying and segmenting a plurality of sequential colored images.

Referring now to FIG. 10, the movement module 740 is partially illustrated. The movement module 740 includes an image colorizer module 1010. The image colorizer module generates successive colors for successive images. That is, in the present example, the objects in a first image are color red as illustrated in FIG. 8. In FIG. 9, the second image has the objects colored green and in a third image, the objects are colored blue, of course multiple set of images can continually be generated and compared and therefore there is no limit to merely three images in the representation above.

An image composite module 1012 is used to overlap the images. By overlapping the images, the color of the objects may change as illustrated in FIG. 9. The color of the objects indicate the position at a relative time. A movement determination module 1014 is thus able to determine the movement and the speed of the movement. Because measurements may be taken based on the position and the time of each image is known, the speed of the movement is determined. The movement determination module 1014 may also determine a type of movement. That is, biofilms typically do not move. By tracking the movement or positions and the time of the images, movement is determined. Determining movement allows differentiation of biofilms from other structures similar that do move. The image processor 62 has a classification module 744 that uses the movement, speed or other characteristics of the object to classify/segment a biofilm. The classification module 744 may be trained processor that uses artificial intelligence to determine various types of biofilm within the image. That is, once the non-moving objects are determined, image recognition using image models may be used to distinguish between biofilm and non-biofilm objects. Eliminating moving object candidates reduces the overall time of the process because recognition does not have to be performed on moving objects.

A display interface 746 is used for controlling the display 64. The display interface 746 generates a classification signal that may result in the display 64 generating a message that the biofilm is a particular type of biofilm. A report such as that illustrated FIG. 6 may be generated by the report generator 748.

Figure 11:
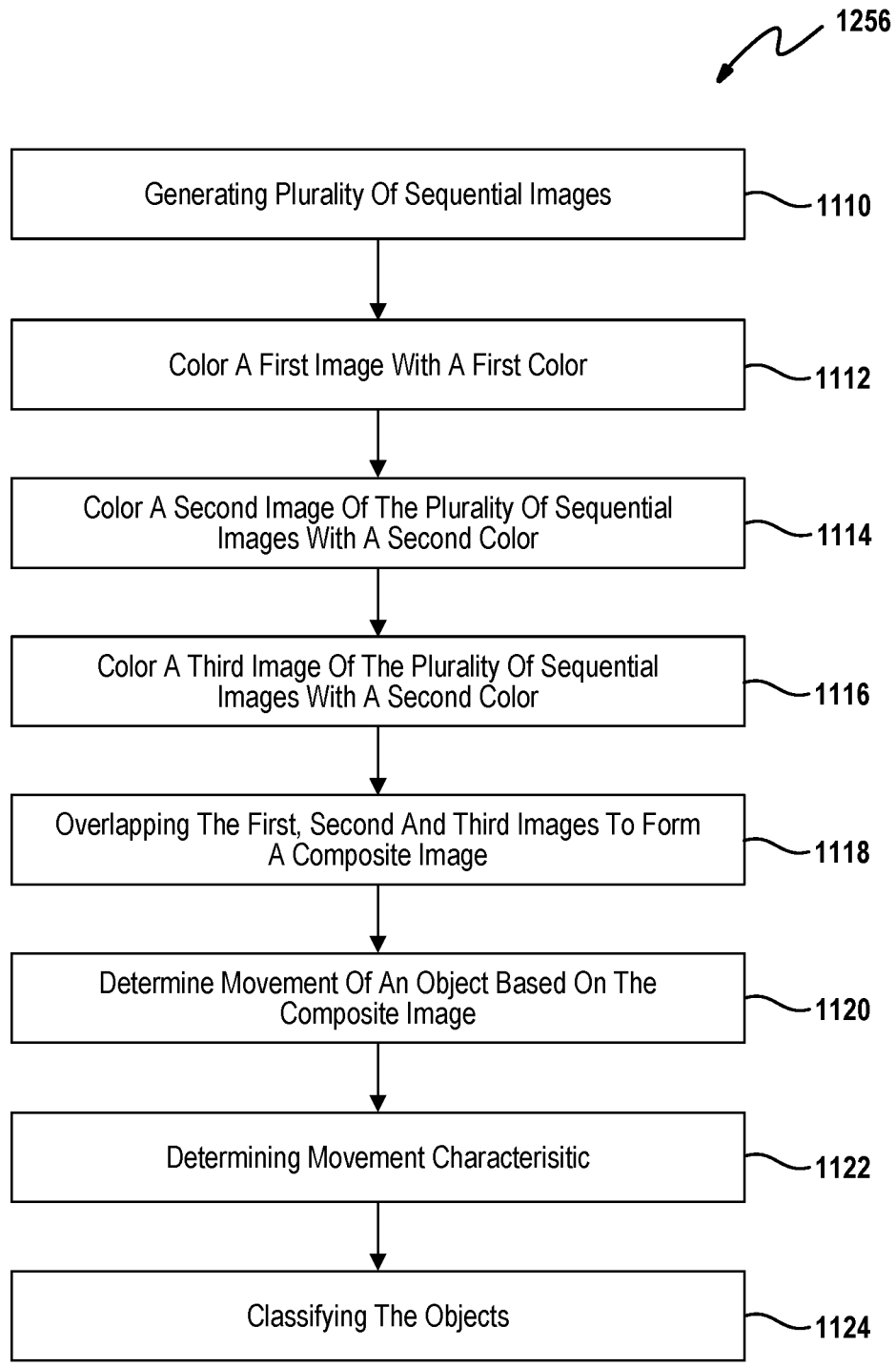
FIG. 11 is a flowchart of a method for operating the system of FIG. 11.
Figure 12:
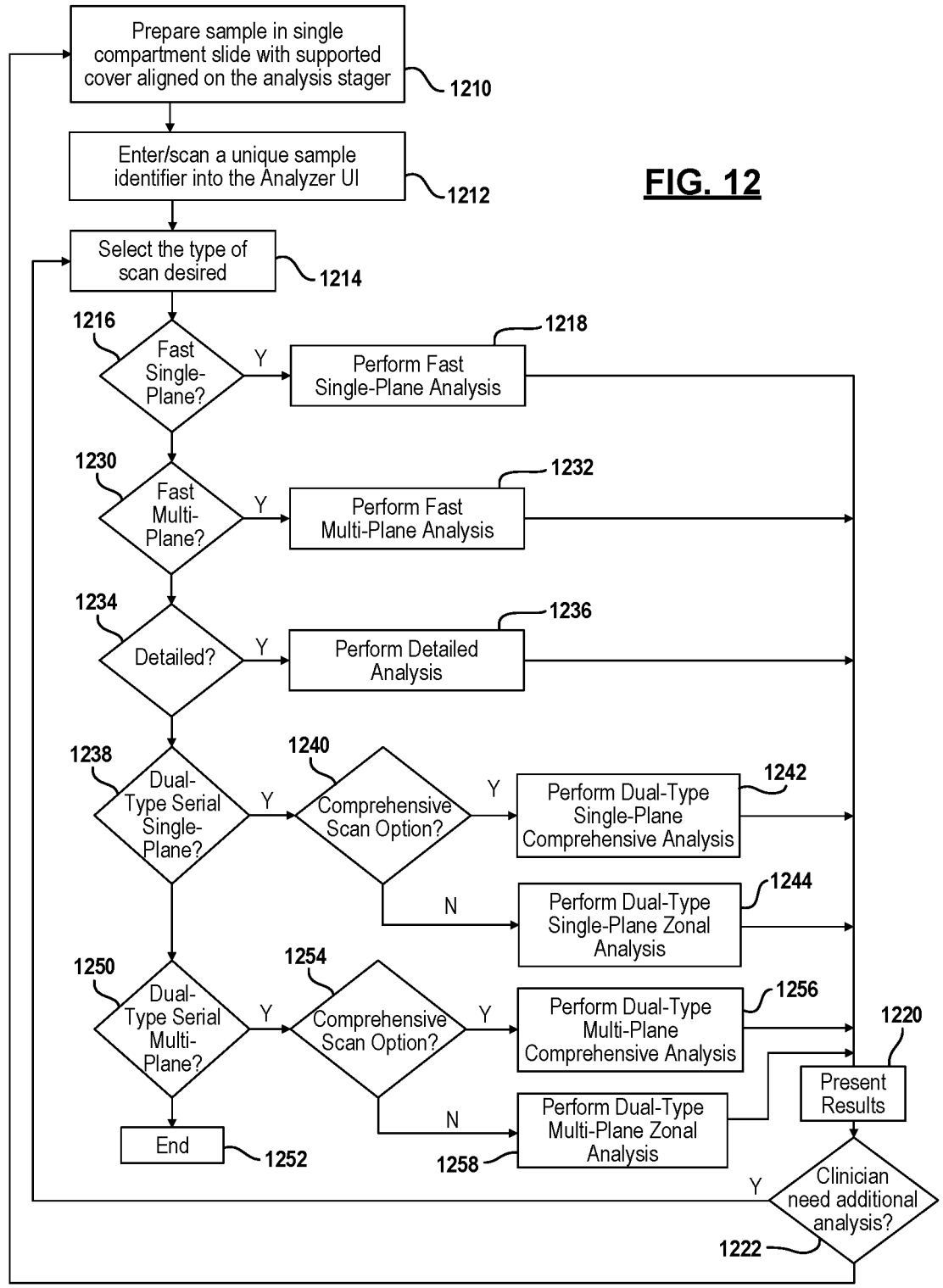
FIG. 12 is a flowchart of a method of operating the analyzer system.

Referring now to FIG. 11, a method for operating the system of FIG. 12 is set forth. In step 1110, a plurality of sequential images is generated. The plurality of sequential images may be generated on a regular basis such as a predetermined number of milliseconds or seconds or minutes apart. In step 1112, a first image is colored with a first color to form a first colored image. In step 1114, a second image of the plurality of sequential images is colored with a second color to form a second colored image. In step 1116, a third image of the plurality sequential images is colored with a second color. In step 1118, the first, second and third colored images are overlapped to form a composite image. The overlapping may be performed using digitally adding techniques. In step 1120, the movement of a structure or object is determined based upon the composite image. That is, by knowing the time between the images and the measurement of the distance between portions of the object within the images, a movement characteristic such as speed, position and the type of movement are used to determine a movement characteristic in step 1122. The type of movement may include repetitive movement in a certain direction and back again. In step 1124, the biofilm is classified based upon the movement characteristic (lack of movement). Other means of forming a classification including the size of the object or portions of the object may also be used.

Referring now the FIG. 12, a method for operating a system is set forth. The analyzer as mention above may be set forth in a preconfigured manner. However, a clinician may use the user interface to enter the type of scan and other information. In the present example, the system 10 has a microscope image capture setup with various user selectable options as well as system design options. The user selectable options are options which the technician or user chooses when operating the system, while system design options are options which the user does not have direct control over.

The system design options include, but are not limited to image colorization, scan sequence, and capture mode. The user selectable options include, but are not limited to scan types and customizable options within scan types.

Image colorization option specifies whether the image colorization algorithm is applied. The fields of view (FOVs) acquired with image colorization turned on will be colorized where pixels values have changed from one image to the next. The colorization algorithm provides an additional feature to the image processor 62 to make decisions. The colorization roughly represents where movement has occurred from one image to the next. As described above, the colorized images are derived from sets of the consecutively captured images across a specified time interval for the same field of view (FOV). A video capturing images may be used. The segmenter may obtain usable images of a particular field of view. In the alternative, if the scan type is Detailed or a Dual-Type Serial, the image capture system may be paused a moment and remain stationary for a period of time to acquire images at each FOV in order to capture multiple images that will be grouped into sets and converted to colorized images. Images that are converted to colorized images should not be acquired while the FOV is changing because certain objects, including biofilm, do not move. The lack of movement is an identifiable characteristic of biofilm and other structures, so it is vital the image capture system is able to differentiate between movement and lack of movement in the field of view. Image colorization takes longer to process than when image colorization is turned off. Despite being slower, image colorization provides important movement features in a way that is more efficient and more informative than traditional movement calculations. Traditional movement calculation algorithms involve complex calculations measuring the distances between one image to the next to determine how far objects have moved. The calculation becomes more difficult with irregularly shaped objects moving in irregular patterns. With image colorization, the shape and pattern of movement are easily captured and displayed with colorized effects directly onto the resultant FOV. This enables the image processor to use the colorized pattern information as a feature to train a machine-learning algorithm.

The scan sequence option specifies the sequence of capture in multi-plane scanning, as described below. There are two options: horizontal and vertical. In a horizontal scan sequence, the FOVs captured by the image capture system are acquired first along the X and Y axes across a single plane or depth. Then, the depth is changed (change in Z axis) to access a different plane. In other words, the distance between the camera and the sample holder is changed to observe the sample holder at a greater or shorter distance. After the change in the Z axis has occurred, the image capture system makes changes in the X and Y axes to capture images across the entire plane. The process can be done repeatedly at multiple planes or depths to acquire a three-dimensional FOV capture of the entire sample holder. In a vertical scan sequence, images are captured at one FOV at a particular X and Y-axis, then the Z axis is changed to acquire images at different planes within the same X and Y axis. Once all FOVs have been captured at each Z axis, the X and Y axes are changed to allow the image capture system to acquire images at a new location. Once at the new location, the Z axis is once again changed to acquire images at each plane within the same X and Y axis. The process is repeated to acquire a complete three-dimensional FOV capture of the entire sample. In any scan sequence, the position of each field of view is known allowing the fields of view to be stitched together to form the scan area.

The capture mode specifies whether images are captured during the scanning process as individual images or as continuous video. The first option allows images to be captured as rapid stills at a frequency, which can be configurable at a system design. The second option allows the image capture system to take continuous video at a variable frame rate. If the second option is used, the video will be fragmented into still images either for direct analysis by the image segmentation analyzer (if image colorization is turned off) or to be sent in sets of three at consecutive frames for colorization when image colorization is turned on.

To start the process in step 1210, a sample is prepared in a single compartment sample holder with a supported cover that is aligned on the analysis stager. As mentioned above, the volume of the fluid may be known based upon the single compartment sample holder. However, as mentioned above, the type of sample holder may vary and thus a process for calibrating the amount of volume within the well may be provided.

In step 1212, a clinician enters or scans a unique sample identifier into the analyzer using the user interface 74.

In step 1214, a clinician selects the type of scan desired. Various types of scans may be performed including a fast, single plane scan, a fast, multi-plane scan, a detailed scan, a dual-type serial single-plan scan or a dual type serial-multi-plane scan. As mentioned above, the scan types may be user selectable.

The fast, single-plane scan is the fastest type of scan set forth. The fast single plane scan provides a quick scan in a single plane of a microscope sample holder. As mentioned above, a plane is a horizontal layer of the sample holder. Each sample holder may have multiple planes or layers of scan performed. The fast, single-plane scan captures images along a single plane through changes in the X and Y axes only. The area of the objects detected may be determined. The goal of the present scan type is to get a snapshot of the sample as quickly as possible to get a response from the analyzer to determine if biofilm is likely present in the sample. To expedite the scanning process, image colorization is also not used since pausing the image capture system at each FOV is involved and processing the colorized images that slows the scanning process.

The fast, multi-plane scan is the next fastest option. Like the fast single-plane scan, it does not use image colorization. However, it performs a multi-plane scan of the sample, which takes longer than a single-plane scan. In a multi-plane scan, the image capture system captures images along multiple planes of the sample rather than along a single plane. This provides a capture of the sample holder that is still fast but is more detailed since it returns a three-dimensional layout of the sample holder. The scan sequence determines how the three-dimensional layout is acquired. Three multi-plane scans can either be done in a horizontal or vertical sequence.

An enhancement to the fast, single-plane scan fast and the multi-plane scan processes is interleave scanning. The present technique dynamically applies image colorization in real-time when biofilm is flagged. The advantage to applying image colorization in real-time rather than in a follow-up scan is that samples degrade and change over time. For example, if a user performs a fast scan and the image processor flags some of the FOVs as biofilm, the user may want to perform a more detailed scan to get more information. However, by the time a more detailed scan has been performed, the quality of the sample may have degraded or objects within the sample holder may simply have moved. In the present enhancement, the FOVs are sent to the image processor in real-time during the fast scan. During a fast scan, image colorization is not used, so there is minimal processing required before the FOVs are sent to the processor. However, once biofilm have been flagged, image colorization would be turned on to capture colorized images of suspected biofilm.

The detailed scan type is slower than the two preceding scan types because it uses multi-plane scanning along with image colorization. The user can choose the detailed scan type if a more detailed capture of the sample holder is desired at the expense of time.

The dual-type serial scan type is the slowest scan available and the most complex, but potentially the most complete. It combines the fast and detailed scans and comes with various sub-options to customize the scan. If the user chooses the dual type serial scan, they will select whether to start with a fast, single-plane scan (scan type 1) or fast, multi-plane scan (scan-type 2). Then, the user will choose whether to combine the fast scan with a comprehensive or zonal scan. The Comprehensive scan is a multi-plane scan with image colorization turned on (identical to Scan Type 3). The zonal scan is a multi-plane scan with image colorization, but it only performs the multi-plane, colorized scans at zones, which have been flagged during the fast scan as possibly having biofilm. This allows the zonal scan to be more precise and targeted than the comprehensive scan and potentially faster. However, one downside to the zonal scan is that it is possible for the image capture system not detect biofilms since it only performs a detailed scan of zones that were flagged during the fast scan. The comprehensive scan, meanwhile, may find additional biofilm that were missed during the initial fast scan since it performs a detailed scan of the entire sample regardless of what the fast scan captured.

In step 1216, it is determined whether a fast, single-plane test has been selected. If a fast single-plane test has been selected, step 1218 performs a fast, single-plane analysis for the sample corresponding to the sample identifier. Thereafter, step 1220 presents the results and step 1222 determines whether a clinician needs additional analysis. When additional analysis is needed, step 1214 is again performed. When the clinician determines that additional analysis is not needed, step 1210 is performed.

Referring back to step 1216, when fast, single-plane analysis is not selected, step 1230 determines whether fast, multi-plane scanning is selected. When fast, multi-plane analysis is selected, step 1232 performs fast, multi-plane analysis. After step 1232, steps 1220 and 1222 are again performed.

Referring back to step 1230, when fast, multi-plane scanning is not selected, step 1234 determines whether detailed scanning has been selected. When detailed scanning has been selected in step 1234, step 1236 performs detailed analysis. After step 1236, step 1220 and 1222 are again performed.

Referring back to step 1234, when detailed analysis is not selected, step 1238 determines whether a dual-type serial single—plane scanning has been selected. When dual-type serial single-plane scanning has been selected, step 1240 determines whether a comprehensive scan option has been selected. When the comprehensive scan option has been selected, step 1242 performs a dual-type single-plane comprehensive analysis. In step 1240, when comprehensive scan option has not been selected, step 1244 performs dual-type single-plane zonal analysis. After step 1242 and 1244, steps 1220 and 1222 are again performed.

In step 1238, when the dual-type, serial single-plan scan has not been selected, step 1250 is performed. In step 1240, if the dual-type serial multi-plane scan has not been selected, step 1252 ends the process. In step 1250, when the dual-type serial multi-plane scan has been selected, step 1254 is performed. In step 1242, it is determined whether a comprehensive scan option has been selected. When a comprehensive scan option has been selected, in step 1254, step 1256 performs dual-type multi-plane comprehensive analysis. In step 1254, when comprehensive scan option has not been selected, a dual-type multi-plane zonal analysis is performed in step 1258. After steps 1256 and 1258, step 1220 is performed.

Figure 13:
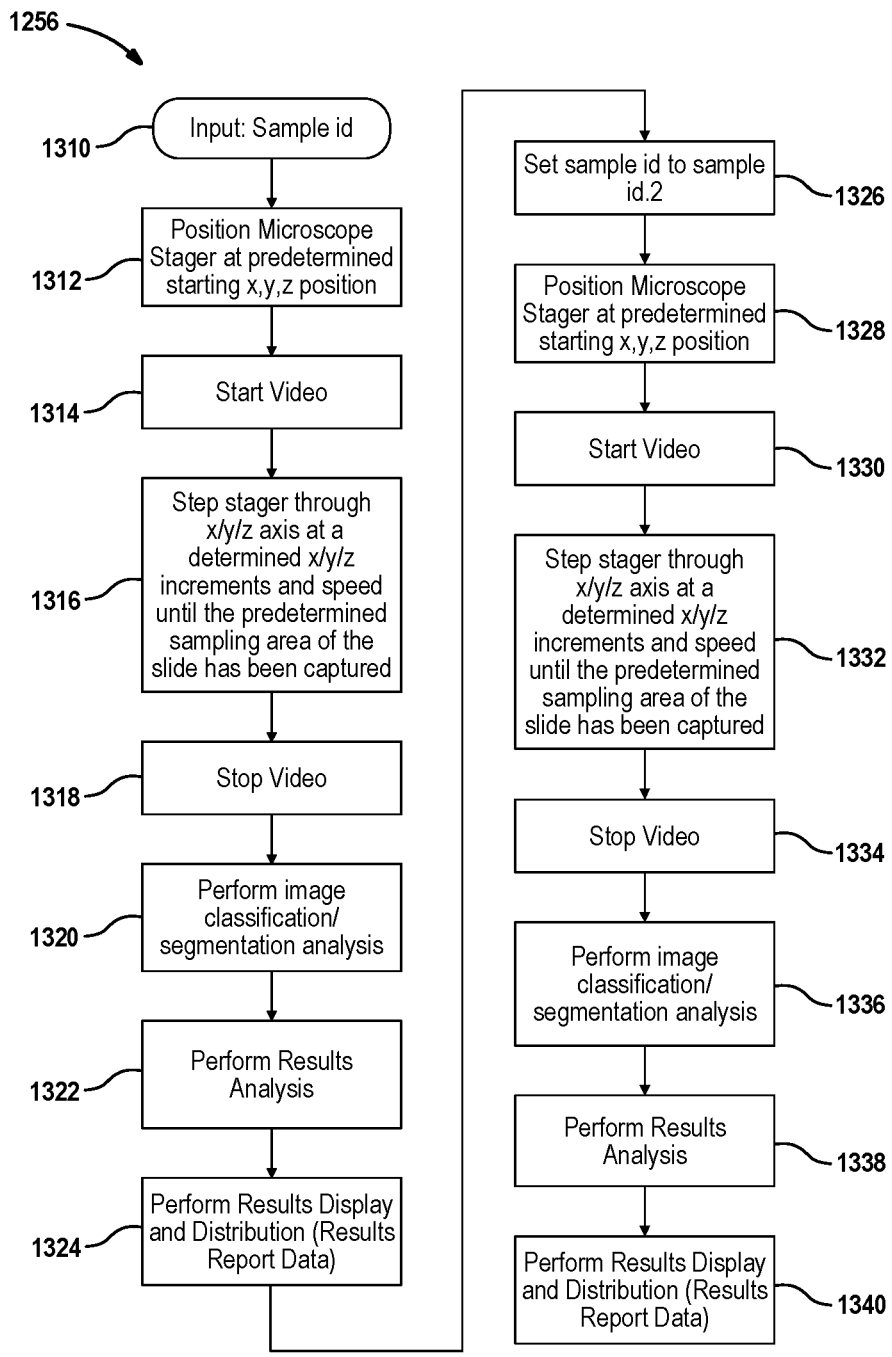
FIG. 13 is a flowchart of a method performing different types of comprehensive analysis of the sample.

Referring now to FIG. 13, the dual-type multi-plane comprehensive analysis step of FIG. 1256 is described. However, the other types of analyses are similar and the differences will also be described herein.

In step 1310, a sample identifier is input to the analyzer. In step 1312, the microscope stage is positioned at a predetermined X, Y and Z position.

In step 1314, starting a video to store the screens is started. In step 1316, the process proceeds by stepping the stager through X, Y and Z axes at predetermined X, Y and Z increments and speed until the predetermined sampling area of the sample holder has been captured. For the fast, single-plane analysis or the dual-type single comprehensive analysis, only X and Y movements are performed in step 1316. In step 1318, the video is stopped. In step 1320, the image is classified and segmented. In the present example, the video is used along with multi-plane, colorization, dual multiple and comprehensive planes is performed. For fast single-plane analysis, only a single plane with no colorization or augmentation is performed. For fast multi-plane analysis, again no colorization is performed. In the detailed scan analysis, colorization is performed on a multi-plane. In a dual-type single plane comprehensive analysis, no color is used.

In step 1322, the results analysis are performed on the classification and segmentation performed in step 1320. Of course, different types of scans provide different types of data and thus different types of speed for the process.

In step 1324, the results are displayed and a report may be generated in step 1324.

In the present example, a dual-type multi-plane comprehensive analysis is performed. The fast single-plane analysis, fast multi-plane analysis and detailed analysis only perform steps 1310 through 1324. Similar steps in a single plane are performed by the dual-type single-plane comprehensive analysis.

In step 1326, a second identifier is used for a second sample to be used. In step 1328, the stager is repositioned at the pre-determined starting position having X, Y and Z coordinates. The same starting positions may be used as in step 1312.

In step 1330, the video is started for obtaining the various images. In step 1332, the process proceeds by stepping the stager through X, Y and Z axes at predetermined X, Y and Z increments and speed until the predetermined sample holder area has been captured. The sample volume ultimately is captured during step 1332 because multi-planes are analyzed. In step 1334, the video is stopped when all of the field of views of the scan area have been obtained. In step 1336, image classification is performed on a multi-plane colorization and dual multi-plane comprehensive analysis. In step 1338, the results from step 1336 are analyzed. In step 1340, the results may be displayed on a display and distributed through the distribution interface. The difference between the dual-type multi-plane comprehensive analysis and the dual-type single-plane comprehensive analysis is that the stager only steps through X and Y positions while maintaining a single plane in the dual-type single-plane comprehensive analysis.

Figure 14:
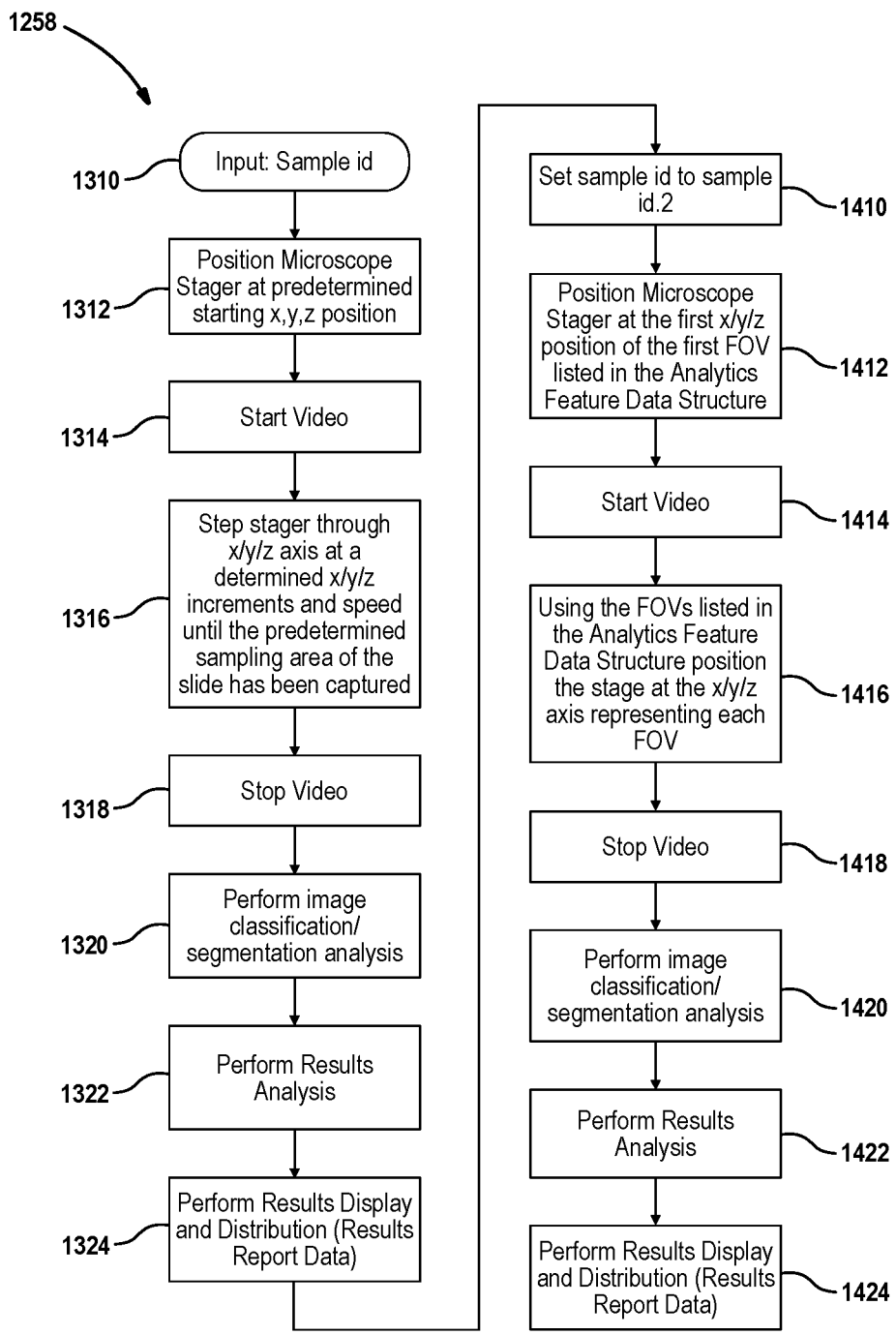
FIG. 14 is a flowchart of a method for performing zonal analysis of a multi-plane sample.

Referring now to FIG. 14, the dual type multi-plane zonal analysis step 1258 of FIG. 12 is set forth in further detail. Steps 1310-1324 are repeated of FIG. 13 are repeated and therefore not repeated. However, step 1320 may be performed with or without colorization. In step 1316, only X and Y axes may be stepped through. However, in this example, step 1410 enters a second identifier to sample. In step 1412, a microscope is positioned at the first X, Y and Z position of the first field of view listed in the analytics feature. In step 1414, the video is started. In step 1416, the field of view listed in the analytics feature structure positions the stager at the X, Y and Z position set forth therein. In step 1418, the video is stopped. Image classification segmentation is performed in step 1420. Colorization may be used in the multi-plane analysis. In step 1422, the results are analyzed using the analytics data and multi-plane colorization. In step 1424, the results are displayed and distributed as mentioned above in step 1340.

Figure 15:
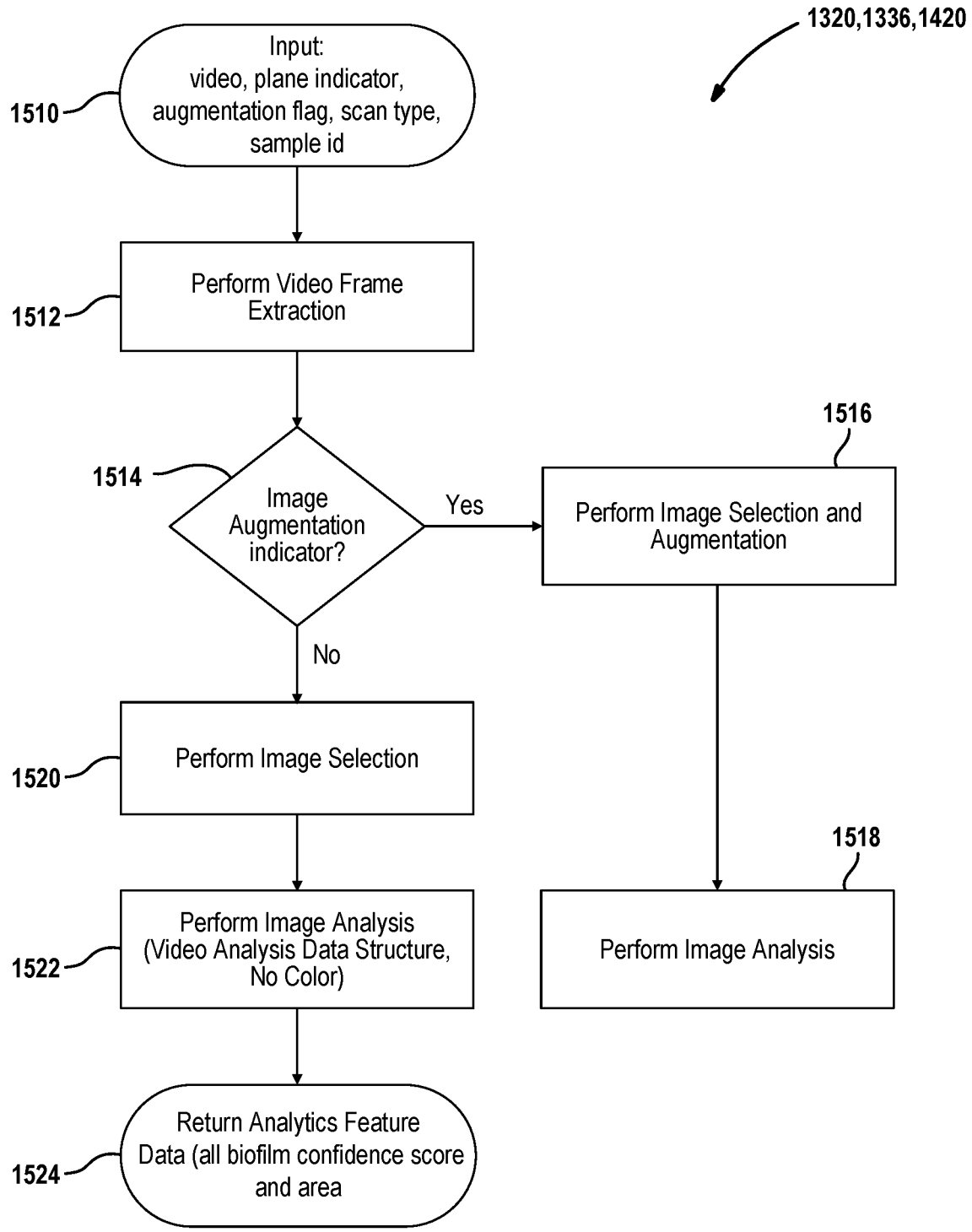
FIG. 15 is a flowchart of a method for classification and segmentation.

Referring now to FIG. 15, the image classification and segmentation steps 1320, 1336 and 1420 of FIGS. 13-14 are set forth in further detail. That is, step 1320 of FIG. 13 is described in further detail. In step 1510, the inputs to the image classification and segmentation are the video, a plane indicator, an augmentation flag as to whether augmentation such as coloration or another type of augmentation has occurred, a scan type and a sample identifier. Other types of augmentation include but are not limited to geometric types like flipping, rotating, cropping the image or enhanced pixel translation techniques like optical density. In this example, augmentation such as photometric (color space) transformation include examples like contrast plus a percent, histogram equalization, white balance, and sharpening using various kernel filter techniques. In step 1512, video frame extraction is performed. The video starts recording and the sample remains stationary for a period of time and then is moved to another location. Once the period of time has elapsed, the stager moves the sample holder in the X and Y axes so that the camera can view a different field of view of the sample holder. Images such as during the video may continue to obtain images even during the movement where they are unused. The sample holder thus remains stationary during brief periods so that a clear image is obtained. Ultimately, the movement and stopping is performed continually to allow the sample to stop moving a clear video or frames of video are taken and movement then occurs. The movement where the sample and the sample holder are not moving is the best position to obtain a clear image.

In step 1514, it is determined whether an image augmentation indicator is set. When the image augmentation indicator is set, step 1516 is performed. Image selection and augmentation is performed in step 1516. Multiple images from different times are aligned to select the images in step 1516. In step 1518, image analysis is performed on the colorization images.

Referring back to step 1514, when no image augmentation indicator is found, step 1520 is performed. In step 1520, image selection is performed. In step 1522, image analysis is performed for the images that were selected in step 1520. In step 1524, analytics are biofilm may be performed as well as obtaining a confidence score in an area of the biofilm.

Figure 16:
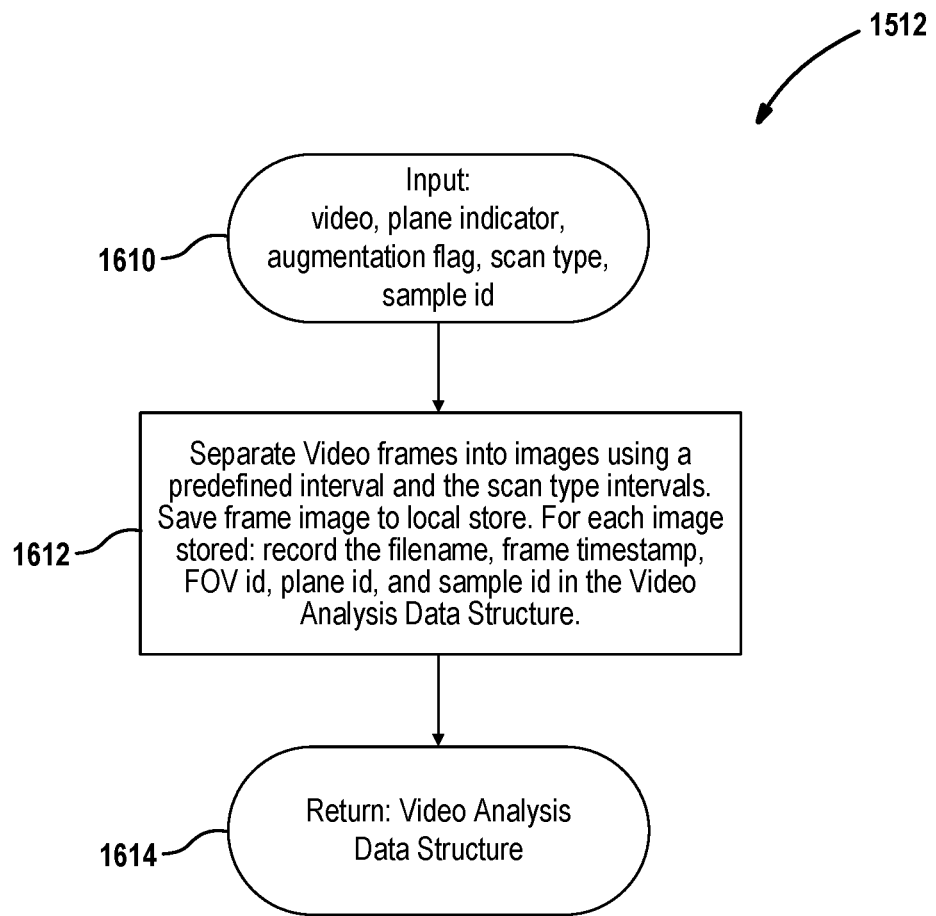
FIG. 16 is a flowchart of a method for video frame extraction.

Referring now to FIG. 16, the video extraction of step 1512 is set forth in further detail. In step 1610, various inputs such as the video, a plane indicator, an augmentation flag, a scan type and a sample identifier are provided. In step 1612, separate video frames are converted into images using a predetermined interval and scan type for the intervals. The frames are stored in a memory or "local store" for each frame record. The file name and a frame timestamp as well as a field of view identifier, a plane identifier and sample identifier are also stored. In step 1614, a video analysis data structure is obtained. The video frames are separated to obtain still images from portions of the video where it is known that the sample or the sample holder are not moving. That is, the sample has settled as well as no movement of the sample holder are used to obtain the separate video frames. Ultimately, the separate video frames are used to obtain images for the entire scanned area. For multi-plane scans, the frame extractor will know the relative time offset when a new field has been positioned. Also, for multi-plane scans, the scan type will group the field of view as stacks of fields of views and assume that all of the stacks will have the same field of view identifier with a plane identifier being used to distinguish the different images in the stack.

In addition, during the process, blurry images are also filtered out and not used. There are software utilities for accomplishing this such as the OpenCV library written in Python that detects blurry images from non-blurry images by analyzing the variance of pixels around the edges of objects.

Figure 17:
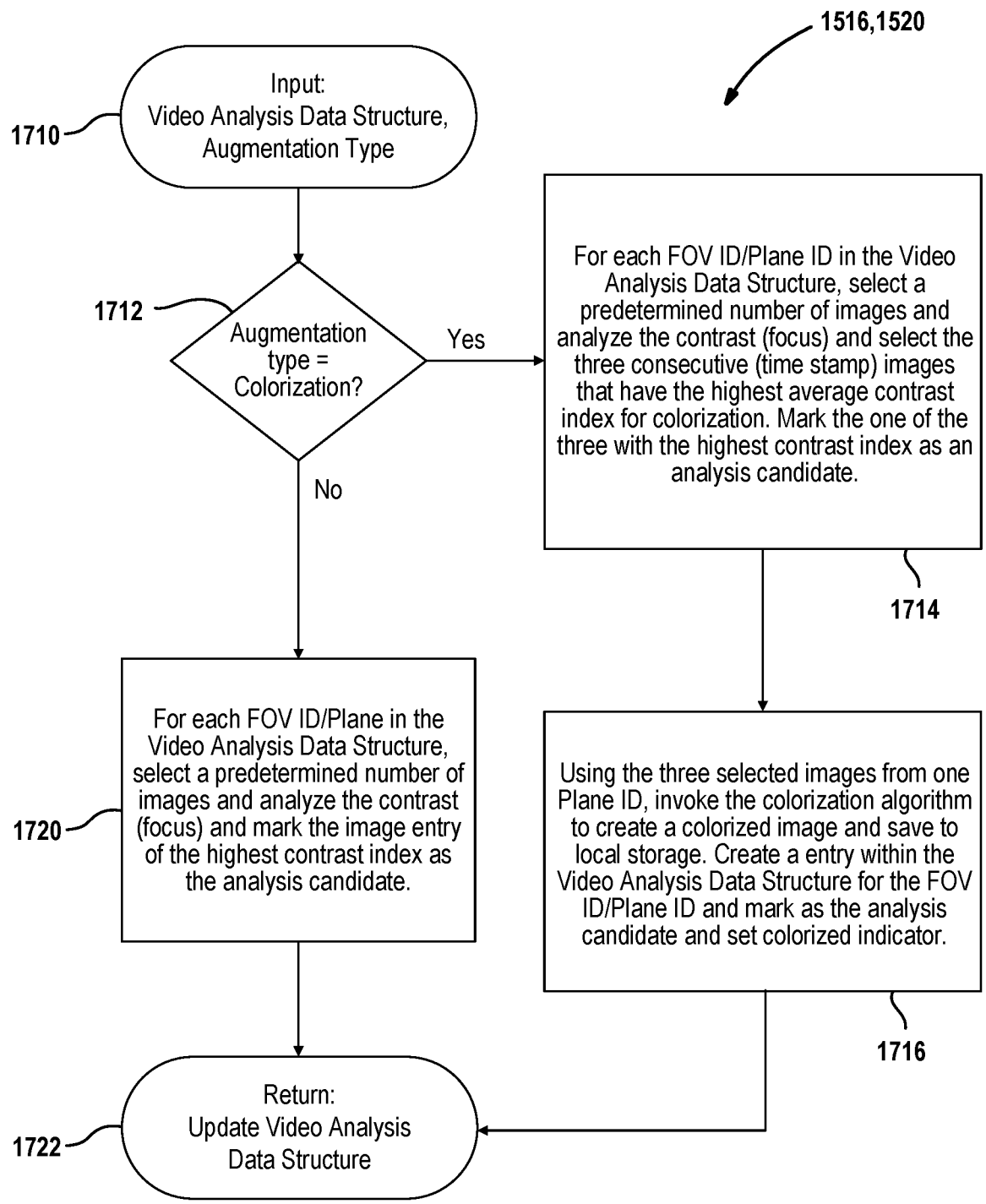
FIG. 17 is a flowchart of a method for image selection and augmentation.

Referring now to FIG. 17, the image selection and augmentation step of step 1516 and 1520 of FIG. 15 is set forth. In step 1710, the video analysis data structure obtained in FIG. 16 is used along with the augmentation type. In step 1712, if the augmentation type is colorization, step 1714 is performed. In step 1714 for each field of view identifier and plane identifier in the video analysis data structure, a predetermined number of images are used for analyzing the contrast (focus) and select the three consecutive time-stamped images that have the highest average contrast index for colorization. The one of the three with the highest contrast index as an analysis candidate is marked. In step 1716, ultimately the three selected images are combined and converted into a single colorized image using the colorization scheme described above. The result in colorized image shows colorization where pixel values have been changed from one image to another. When the pixel values have changed, indicating movement. Ultimately, the colorized image is saved to local storage in step 1716. An entry within the video analysis data structure is used for the field of view and plane identifier. The image may be marked as an analysis candidate with the colorized indicators set. Because biofilm does not move, images of the biofilm should be in black, gray and white with no color. This allows the system to distinguish between biofilms and structures that appear similar to biofilms such as macrophages.

Referring back to step 1712, when there has been colorization as the augmentation type in step 1712, step 1720 is performed. In the present example, the field of view identifier and plane identifier are used to select a predetermined number of images and analyze the contract (focus) and mark the image entry of the highest contrast index as the analysis candidate. After step 1716 and 1720, step 1722 returns the updated video analysis data structure to the system so that other types of data may be obtained. For the image analysis in step 1812, it is determined whether the image augmentation indicator is indicating colorization. When colorization is indicated in step 1812, step 1814 is performed. In step 1814, each image marked as an analysis candidate is communicated to the image processor for classification and segmentation. An entry for the field of view identifier, plane identifier, a colorized indicator, a sample identifier and the analytic results are communicated to an analytics feature data structure stored in the memory.

Referring back to step 1812, when the augmentation indicator does not indicated colorization, step 1816 submits each image to the image processor for classification/segmentation for the non-colorized model. Each of the images has an entry for the field of view, the plane identified, the colorized indicator, a sample identifier, and the analytic results that are provided to the analytics feature structure and stored in the memory. In step 1818, the analytics feature and data structure is returned. All the biofilm identifiers, the confidence scores, the areas of the biofilm, the biofilm center locations, the field of view, the plane identifier, colorized indicator and sample identifier are all stored within the analytics feature data structure.

Figure 18:
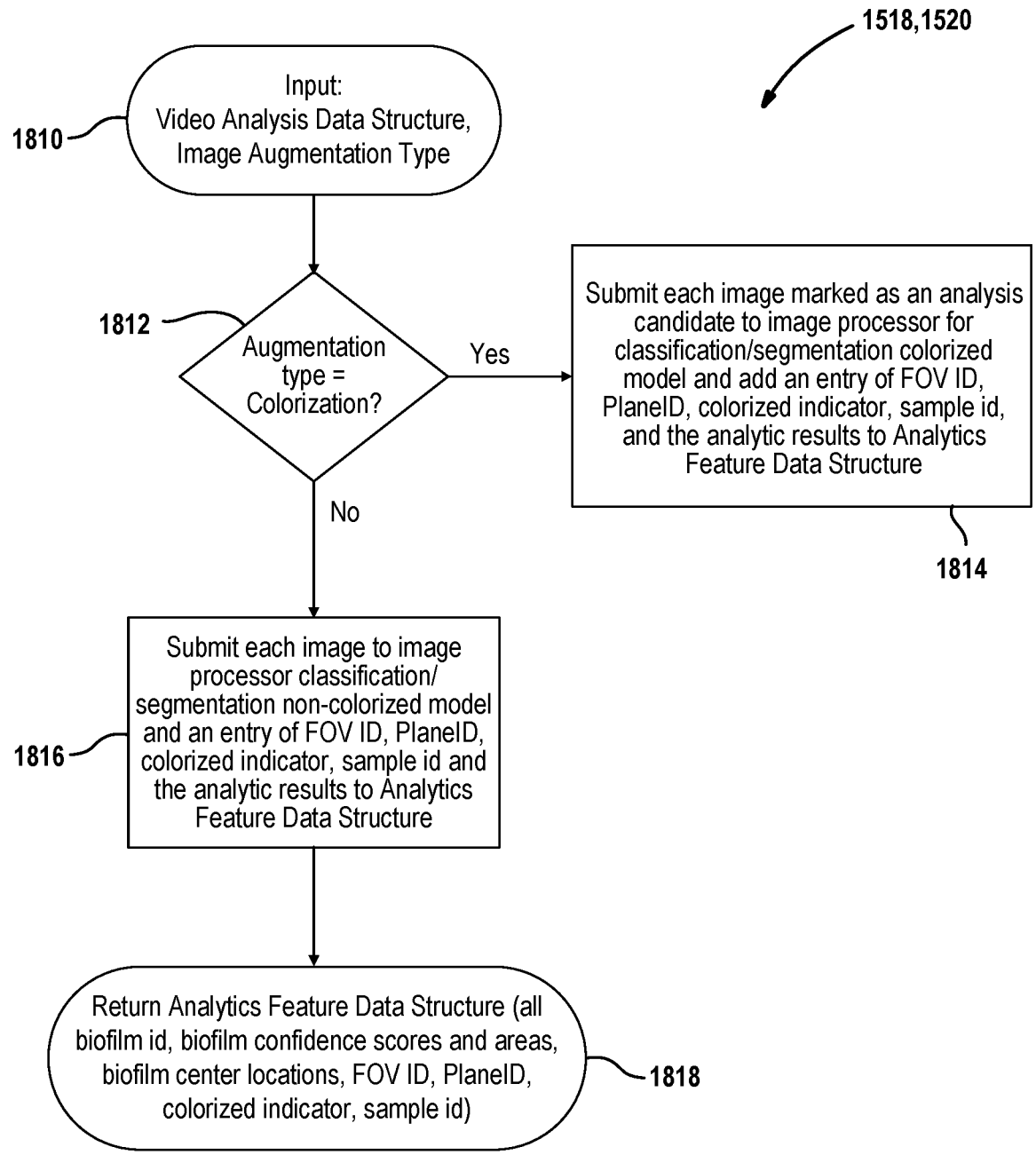
FIG. 18 is a flowchart of a method for image analysis.
Figure 19:
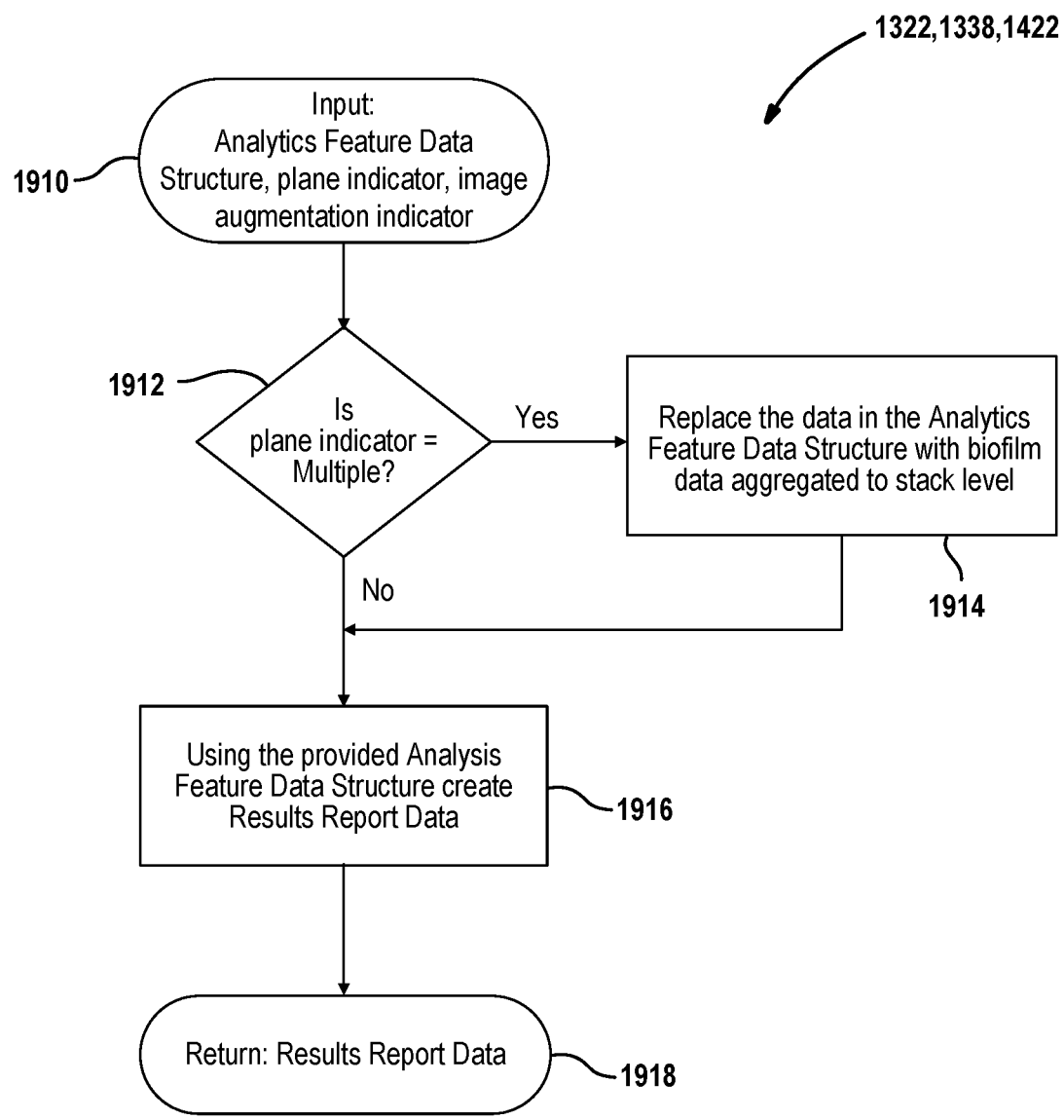
FIG. 19 is a flowchart of a method for performing results analysis.

Referring now to FIG. 19, steps 1322 and 1338 of FIG. 13 and step 1422 of FIG. 14 are set forth in further detail. In step 1910, the analytics feature data from FIG. 18 is provided as well as a plane indicator, and an image augmentation indicator. In step 1912, if the plane indicator is multiple, step 1914 is performed which replaces the data in the analytics feature data with biofilm aggregated to the stack level. In step 1912, if the plane indicator is not multiple and after step 1914, step 1916 uses the provided analysis feature data to create a report for a report data. In step 1918, the report data is return to the analytic system. The analytics feature described above is the confidence scores of the biofilm and the areas. The biofilm center location and the field of view of the biofilm as well as the biofilm identifier are all provided. The report may provide the data set forth in FIG. 6.

Figure 20:
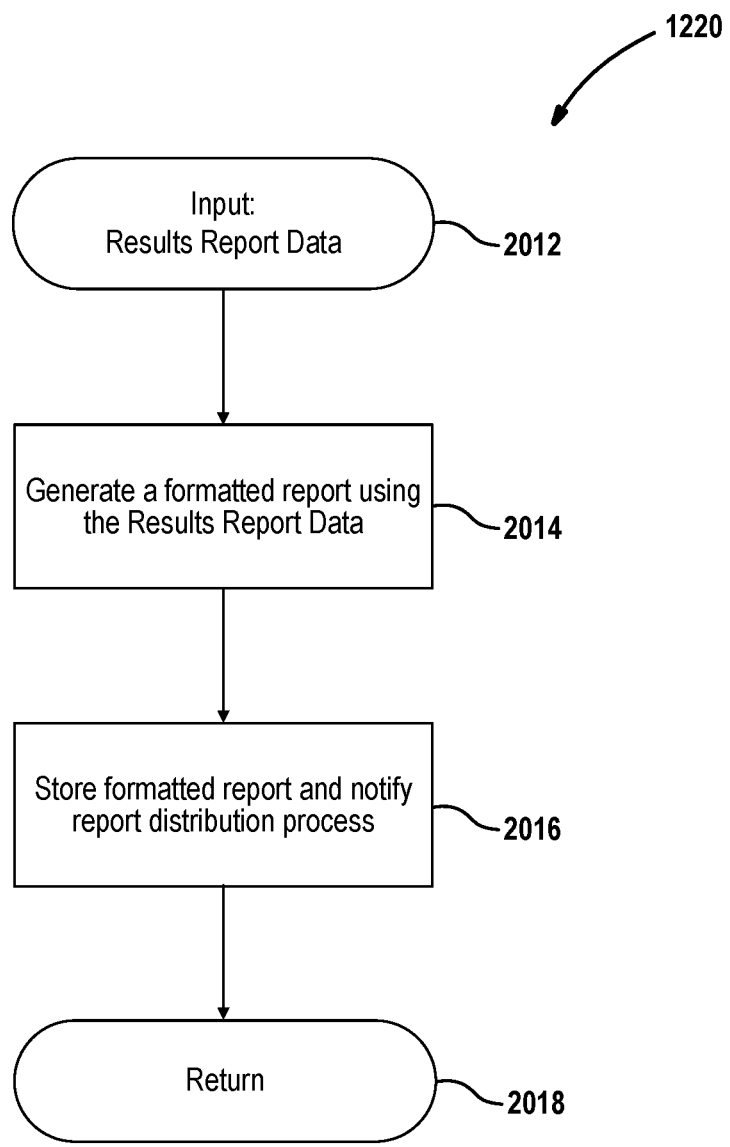
FIG. 20 is a flowchart of a method for displaying and distributing the results.

Referring now to FIG. 20, step 1220 of FIG. 12 is illustrated in further detail. The results report data from FIG. 19 is provided in step 2012. In step 2014, a formatted report using the results data may be obtained. In step 2016, the formatted report may be generated and stored. The report or availability of the report may be distributed. The system returns in step 2020.

Those skilled in the art can now appreciate from the foregoing description that the broad teachings of the disclosure can be implemented in a variety of forms. Therefore, while this disclosure includes particular examples, the true scope of the disclosure should not be so limited since other modifications will become apparent to the skilled practitioner upon a study of the drawings, the specification and the following claims.

The invention claimed is:

1. A system comprising:
    a sample holder holding a bodily fluid sample;
    an image capture device generating an image of the bodily fluid sample comprising a plurality of fields of view;
    an image processor programmed to
        determine a biofilm in the bodily fluid sample from the image;

determine a biofilm area or volume within each of the plurality of fields of view to form a plurality of biofilm areas;
determine a total biofilm area or total biofilm volume by adding the plurality of biofilm areas;
determine a first value corresponding to a comparison of the total biofilm area or the total biofilm volume and a total volume of the bodily fluid sample; and
classify the first value into a classification; and
an analyzer, in response to the classification, displaying an indicator on a display for indicating the classification of the biofilm within the bodily fluid sample.

2. The system of claim 1 wherein the indicator comprises presence of biofilm.

3. The system of claim 1 wherein the indicator corresponding to a density of the biofilm within the bodily fluid sample.

4. The system of claim 3 wherein the indicator corresponds to a severity based on the density of the biofilm.

5. The system of claim 1 wherein the indicator corresponding to a volume of biofilm within the bodily fluid sample.

6. The system of claim 1 wherein the indicator corresponding to a volume weighted confidence score of the biofilm within the bodily fluid sample.

7. The system of claim 1 wherein the image processor determines an average confidence level and wherein the indicator comprises the average confidence level.

8. The system of claim 1 wherein the sample holder holds the sample in a well with cover, said well and cover comprising a predetermined sample volume.

9. The system of claim 1 further comprising a position actuator positioning the sample holder into the plurality of fields of view.

10. The system of claim 1 wherein the image processor is programmed to determine the biofilm by
obtaining a plurality of successive frames of a field of view;
distinguishing a non-moving object and a moving object from a plurality of objects in the bodily fluid sample based on the plurality of successive frames of the field of view;
classifying the non-moving object as a biofilm; and
generating an indicator in response to classifying.

11. The system of claim 1 wherein the indicator comprises a ratio of a total number of biofilms found to a total volume of the plurality of fields of view.

12. The system of claim 1 wherein the indicator comprises a ratio and variance of the total biofilm volume to a total volume of the plurality of fields of view.

13. The system of claim 1 wherein the indicator comprises average and variance of confidence level of biofilm found.

14. The system of claim 1 wherein the indicator comprises a weighted average and variance of confidence level per biofilm found using a summation of confidence level multiplied by volume for every biofilm found.

15. The system of claim 1 wherein the indicator comprises a weighted average and variance confidence level per biofilm found using a summation of confidence level multiplied by volume for every field of view of the plurality of fields of view.

16. A method comprising:
generating an image of a bodily fluid sample comprising a plurality of fields of view;
determining a biofilm in the bodily fluid sample from the image;
determining a biofilm area or volume within each of the plurality of fields of view to form a plurality of biofilm areas;
determining a total biofilm area or volume by adding the plurality of biofilm areas;
determining a first value corresponding to a comparison of the total biofilm area or volume and a total volume of the bodily fluid sample;
classifying the first value into a classification; and
in response to the classification, displaying an indicator on a display for indicating the classification of the biofilm within the bodily fluid sample.

17. The method of claim 16 wherein displaying the indicator comprises displaying a presence of biofilm.

18. The method of claim 16 wherein displaying the indicator comprises displaying a density of biofilm within the bodily fluid sample.

19. The method of claim 18 wherein displaying the indicator comprises displaying a severity based on the density of the biofilm.

20. The method of claim 16 wherein displaying the indicator comprises displaying a volume of biofilm within the bodily fluid sample.

21. The method of claim 16 wherein displaying the indicator comprises displaying a volume weighted confidence score of biofilm within the bodily fluid sample.

22. The method of claim 16 further comprising determining an average confidence level and wherein displaying the indicator comprises displaying the indicator comprising the average confidence level.

23. The method of claim 16 wherein determining the biofilm comprises:
obtaining a plurality of successive frames of a field of view;
distinguishing a non-moving object and a moving object from a plurality of objects in the bodily fluid sample based on the plurality of successive frames of the field of view;
classifying the non-moving object as a biofilm.

24. The method of claim 16 wherein displaying the indicator comprises displaying a ratio of a total number of biofilms found to a total volume of the plurality of fields of view.

25. The method of claim 16 wherein displaying the indicator comprises displaying a ratio and variance of the total biofilm volume to a total volume of the plurality of fields of view.

26. The method of claim 16 wherein displaying the indicator comprises displaying average and variance of confidence level of biofilm found.

27. The method of claim 16 wherein displaying the indicator comprises displaying a weighted average and variance of confidence level per biofilm found using a summation of confidence level multiplied by volume for every biofilm found.

28. The method of claim 16 wherein displaying the indicator comprises displaying a weighted average and variance confidence level per biofilm found using a summation of confidence level multiplied by volume for every field of view of the plurality of fields of view.

* * * * *